US012616272B2

(12) United States Patent
Dougall et al.

(10) Patent No.: US 12,616,272 B2
(45) Date of Patent: May 5, 2026

(54) GAIT MODIFICATION APPARATUSES, SYSTEMS AND METHODS

(71) Applicant: SCIENTIFIC MOTION TECHNOLOGIES INC., Miami, FL (US)

(72) Inventors: John Dougall, Billingham (GB); Frank Foley, Dorset (GB); Scott Greenberg, Gainesville, FL (US)

(73) Assignee: SCIENTIFIC MOTION TECHNOLOGIES INC., Miami, FL (US)

( * ) Notice: Subject to any disclaimer, the term of this patent is extended or adjusted under 35 U.S.C. 154(b) by 709 days.

(21) Appl. No.: 17/238,385

(22) Filed: Apr. 23, 2021

(65) Prior Publication Data

US 2021/0235809 A1     Aug. 5, 2021

Related U.S. Application Data

(63) Continuation of application No. PCT/US2019/057767, filed on Oct. 24, 2019.

(Continued)

(51) Int. Cl.
*A43B 7/14*          (2022.01)
*A43B 1/10*          (2006.01)
(Continued)

(52) U.S. Cl.
CPC .................. *A43B 7/14* (2013.01); *A43B 1/10* (2013.01); *A61B 5/112* (2013.01); *A61B 5/4833* (2013.01);
(Continued)

(58) Field of Classification Search
CPC ........... A43B 7/14; A43B 1/10; A43B 13/122; A43B 13/14; A43B 13/143; A43B 13/145;
(Continued)

(56) References Cited

U.S. PATENT DOCUMENTS

| | | | | |
|---|---|---|---|---|
| 1,021,142 A | * | 3/1912 | Freeman .................. | A43B 5/18 |
| | | | | 36/7.8 |
| 1,333,737 A | * | 3/1920 | Selz .......................... | A43B 7/14 |
| | | | | 36/172 |

(Continued)

FOREIGN PATENT DOCUMENTS

| | | | | |
|---|---|---|---|---|
| GB | 2134770 A | * | 8/1984 | ............... A43B 5/06 |
| WO | 2015169941 A1 | | 11/2015 | |

OTHER PUBLICATIONS

International Search Report and Written Opinion of the International Searching Authority for International Patent Application No. PCT/US2019/057767 mailed on Jan. 9, 2020.

(Continued)

*Primary Examiner* — Heather Mangine
*Assistant Examiner* — Raquel M. Weis
(74) *Attorney, Agent, or Firm* — Heslin Rothenberg Farley & Mesiti P.C.

(57) ABSTRACT

The disclosure provides gait modification or treatment apparatus, systems and methods that are appropriate for everyday life, have a significant mechanical effect, and provide a mechanism for tracking the compliance and performance of the patient to allow for individualized management of a gait modification prescription or treatment plan or sequence. Gait modification/treatment apparatus, systems and methods utilizing substantially rectilinear projections in the hindfoot and the forefoot are disclosed. Gait modification/treatment apparatus, systems and methods utilizing a projection that defines an engagement surface extending from the hindfoot to the forefoot are also disclosed. Gait modification/treatment apparatus, systems and methods utilizing a non-linear guide rail extending from the hindfoot to the forefoot are also disclosed. Further, gait modification/treatment apparatus, systems and methods utilizing an array of discrete pegs (Continued)

of differing stiffness/compression that provide load instability at least in the hindfoot and the forefoot are disclosed.

34 Claims, 20 Drawing Sheets

Related U.S. Application Data

(60) Provisional application No. 62/750,482, filed on Oct. 25, 2018.

(51) Int. Cl.
A61B 5/00 (2006.01)
A61B 5/11 (2006.01)

(52) U.S. Cl.
CPC ........ *A61B 5/6807* (2013.01); *A61B 2560/04* (2013.01)

(58) Field of Classification Search
CPC ... A43B 13/146; A43B 13/148; A43B 13/223; A61B 5/6807; A61B 5/112; A61B 5/4833; A61B 2560/04
See application file for complete search history.

(56) References Cited

U.S. PATENT DOCUMENTS

| | | | | |
|---|---|---|---|---|
| 1,776,750 | A * | 9/1930 | Burns | A43B 13/12 36/145 |
| 2,311,925 | A * | 2/1943 | Boos | A43B 7/1469 36/DIG. 1 |
| 2,518,649 | A * | 8/1950 | Tydings | A43B 7/24 36/144 |
| 2,616,190 | A * | 11/1952 | Darby | A43B 7/1425 36/144 |
| 2,884,717 | A * | 5/1959 | Goldberg | A43B 13/143 36/169 |
| 3,148,678 | A * | 9/1964 | Roberts | A43B 7/1415 602/29 |
| 3,169,327 | A * | 2/1965 | Fukuoka | A43B 5/007 D2/960 |
| 3,305,947 | A * | 2/1967 | Kalsoy | A43B 13/143 36/144 |
| 3,402,485 | A * | 9/1968 | Mcmorrow | A43B 3/0078 101/368 |
| 3,804,099 | A * | 4/1974 | Hall | A43B 21/24 36/142 |
| 3,936,956 | A * | 2/1976 | Famolare, Jr. | A43B 13/143 36/32 R |
| 3,958,578 | A * | 5/1976 | Tennant | A43B 7/00 482/79 |
| 4,040,192 | A * | 8/1977 | Perez | A63B 69/0028 36/108 |
| 4,041,619 | A * | 8/1977 | Sapper | A43B 13/145 36/103 |
| 4,348,821 | A * | 9/1982 | Daswick | A43B 13/24 36/114 |
| 4,372,059 | A * | 2/1983 | Ambrose | A43B 13/184 36/103 |
| 4,446,856 | A * | 5/1984 | Jordan | A61F 5/0111 602/27 |
| 4,557,059 | A * | 12/1985 | Misevich | A43B 5/06 36/129 |
| 4,694,591 | A * | 9/1987 | Banich | A43B 13/12 36/31 |
| 4,852,273 | A * | 8/1989 | Hamy | A43B 7/141 36/28 |
| 4,875,683 | A * | 10/1989 | Wellman | A63B 69/3673 473/217 |
| 5,138,777 | A * | 8/1992 | Darby | A61F 5/0195 36/110 |
| 5,448,839 | A * | 9/1995 | Blissett | A43B 13/38 36/144 |
| 5,507,106 | A * | 4/1996 | Fox | A43B 13/143 36/114 |
| 5,579,591 | A * | 12/1996 | Kousaka | A43B 13/143 36/31 |
| 5,586,398 | A * | 12/1996 | Carlson | A43B 5/06 36/43 |
| 5,592,757 | A * | 1/1997 | Jackinsky | A43B 13/12 36/31 |
| 5,647,145 | A * | 7/1997 | Russell | A43B 13/188 36/31 |
| 5,826,351 | A * | 10/1998 | Tsuji | A43B 13/148 36/31 |
| 6,183,425 | B1 * | 2/2001 | Whalen | A61B 5/221 600/595 |
| 6,260,289 | B1 * | 7/2001 | Tsuji | A43B 13/145 36/31 |
| 6,523,835 | B1 | 2/2003 | Lyden | |
| 6,782,639 | B1 * | 8/2004 | Muller | A43B 13/145 36/117.4 |
| 6,979,287 | B2 * | 12/2005 | Elbaz | A63B 21/0004 482/148 |
| 8,307,569 | B2 * | 11/2012 | McInnis | A43B 13/203 36/35 B |
| 8,387,278 | B2 * | 3/2013 | Rees | A43B 13/143 36/103 |
| 8,434,244 | B2 * | 5/2013 | Litchfield | A43B 13/203 36/28 |
| 8,533,980 | B2 * | 9/2013 | Elbaz | A43C 19/00 36/15 |
| D693,548 | S * | 11/2013 | Yudelowitz | A43B 13/143 D2/947 |
| 8,758,207 | B2 * | 6/2014 | Elbaz | A63B 23/04 482/79 |
| 8,984,770 | B1 * | 3/2015 | Piontkowski | A43B 7/142 36/102 |
| 9,055,788 | B2 | 6/2015 | Elbaz et al. | |
| 9,357,812 | B2 * | 6/2016 | Elbaz | A43B 7/14 |
| 9,693,927 | B2 * | 7/2017 | Mor | A61H 3/00 |
| 10,092,061 | B2 * | 10/2018 | Adair | A43C 1/04 |
| 10,750,812 | B2 * | 8/2020 | Mor | A43B 7/144 |
| 2002/0026730 | A1 * | 3/2002 | Whatley | A43B 13/36 482/79 |
| 2002/0157279 | A1 * | 10/2002 | Matsuura | A43B 13/143 36/103 |
| 2004/0033874 | A1 * | 2/2004 | Elbaz | A43B 5/18 482/148 |
| 2005/0246924 | A1 * | 11/2005 | Masoodifar | A43B 13/148 36/132 |
| 2005/0268490 | A1 * | 12/2005 | Foxen | A43B 7/1445 36/28 |
| 2006/0090372 | A1 * | 5/2006 | Kim | A43B 5/18 36/25 R |
| 2006/0117603 | A1 * | 6/2006 | Park | A43B 7/146 36/103 |
| 2007/0112285 | A1 * | 5/2007 | Dar | A61B 5/6807 600/595 |
| 2007/0193071 | A1 * | 8/2007 | Gilmore | A61F 5/14 36/180 |
| 2008/0127515 | A1 * | 6/2008 | Lohrer | A43B 13/145 36/43 |
| 2008/0146968 | A1 * | 6/2008 | Hanawaka | A61B 5/0002 600/595 |
| 2009/0077830 | A1 * | 3/2009 | Lee | A43B 13/12 36/108 |
| 2009/0119951 | A1 * | 5/2009 | Hartveld | A43B 13/148 36/114 |
| 2009/0199432 | A1 * | 8/2009 | Park | A43B 7/24 36/25 R |
| 2009/0307925 | A1 * | 12/2009 | Pfister | A43B 7/223 36/43 |
| 2010/0011622 | A1 * | 1/2010 | Abadjian | A43B 13/223 36/114 |
| 2010/0192416 | A1 * | 8/2010 | Rees | A43B 21/24 36/103 |

(56) References Cited

U.S. PATENT DOCUMENTS

| | | | | |
|---|---|---|---|---|
| 2010/0236094 A1* | 9/2010 | Ryu | A43B 13/145 | 36/28 |
| 2010/0325919 A1* | 12/2010 | Elbaz | A43B 7/1445 | 36/103 |
| 2011/0009982 A1* | 1/2011 | King | A61H 3/00 | 623/53 |
| 2011/0072684 A1* | 3/2011 | Stubblefield | A43B 13/122 | 36/28 |
| 2011/0107622 A1* | 5/2011 | Schwirian | A43B 13/122 | 12/146 B |
| 2012/0023774 A1* | 2/2012 | Garcia | A43B 13/148 | 36/31 |
| 2012/0073166 A1* | 3/2012 | Bryla | A43B 13/145 | 36/132 |
| 2012/0096744 A1* | 4/2012 | Goodsmith | A43B 13/145 | 36/103 |
| 2012/0246976 A1* | 10/2012 | Weiler | A43B 13/146 | 36/25 R |
| 2013/0025158 A1* | 1/2013 | Baskerville | A43B 7/14 | 36/83 |
| 2013/0055597 A1* | 3/2013 | Hennig | A43B 7/00 | 434/258 |
| 2013/0067764 A1* | 3/2013 | Riddle | A43B 7/1464 | 36/31 |
| 2013/0116726 A1* | 5/2013 | Mor | A43B 7/1445 | 606/204 |
| 2013/0196829 A1* | 8/2013 | Elbaz | A43B 7/00 | 482/79 |
| 2013/0312292 A1* | 11/2013 | Yudelowitz | A43B 13/143 | 36/25 R |
| 2014/0013617 A1 | 1/2014 | Montross et al. | | |
| 2014/0259800 A1* | 9/2014 | O'Reilly | A43B 7/1485 | 36/25 R |
| 2014/0309692 A1* | 10/2014 | Mor | A61H 39/04 | 606/237 |
| 2014/0317959 A1* | 10/2014 | Elbaz | A63B 21/0004 | 36/88 |
| 2015/0119767 A1* | 4/2015 | Mor | A43B 7/147 | 601/28 |
| 2015/0157089 A1* | 6/2015 | Schumacher | A43B 3/0057 | 36/25 R |
| 2015/0201700 A1* | 7/2015 | Jang | A43B 7/06 | 36/3 B |
| 2015/0351493 A1* | 12/2015 | Ashcroft | A43B 13/18 | 36/132 |
| 2016/0073731 A1* | 3/2016 | Piontkowski | A43B 7/142 | 36/43 |
| 2016/0095384 A1 | 4/2016 | Kraft | | |
| 2016/0239014 A1* | 8/2016 | Piontkowski | A43B 13/145 | |
| 2017/0251757 A1* | 9/2017 | Meschter | A43B 13/184 | |
| 2018/0168279 A1* | 6/2018 | Mor | A43B 13/145 | |
| 2018/0168841 A1* | 6/2018 | Elbaz | A43B 7/1445 | |
| 2019/0053567 A1* | 2/2019 | Thomas | A43B 3/0036 | |
| 2019/0069630 A1* | 3/2019 | Hopkins | A43B 13/141 | |
| 2019/0110918 A1* | 4/2019 | Darby, II | A43B 23/08 | |
| 2019/0343224 A1* | 11/2019 | Dean | A43B 13/184 | |
| 2021/0100312 A1* | 4/2021 | Kim | A43B 7/24 | |
| 2022/0192311 A1* | 6/2022 | Lee | A43B 7/145 | |

OTHER PUBLICATIONS

International Preliminary Report on Patentability for International Application No. PCT/US2019/057767, dated Apr. 27, 2021, 15 pages, International Bureau of WIPO.

* cited by examiner

12/14

12/14

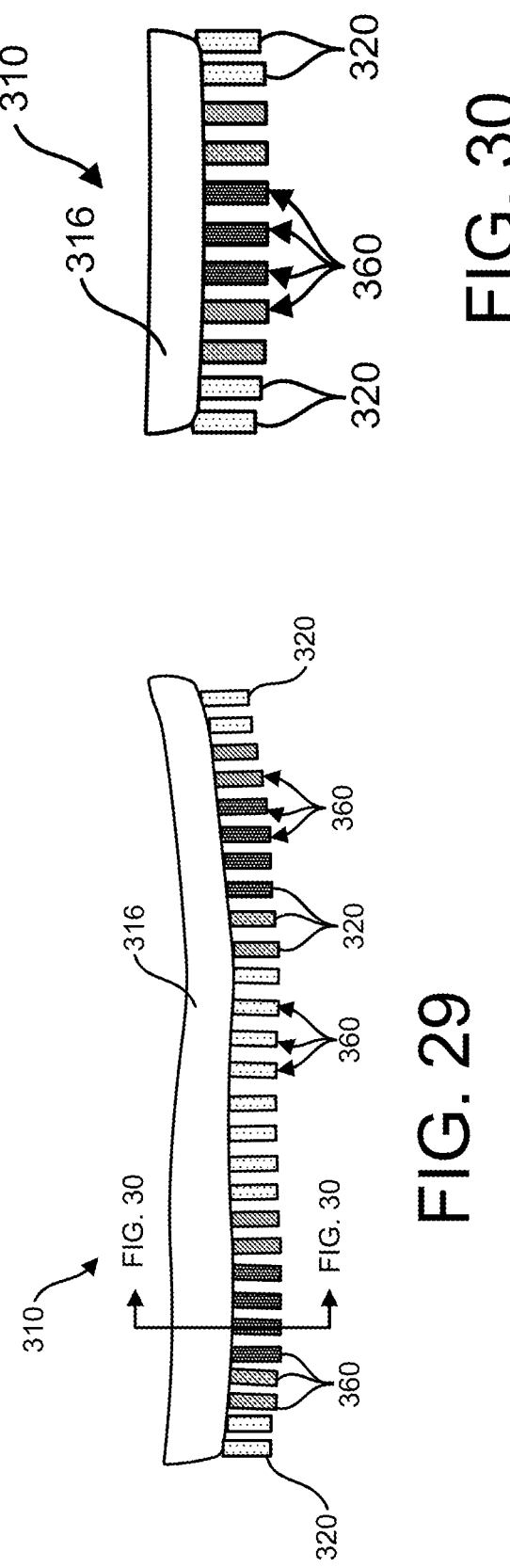
FIG. 30
FIG. 29
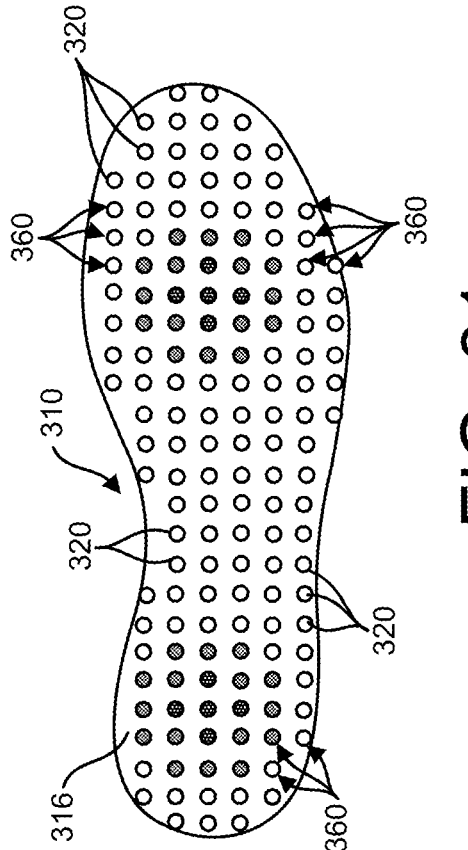
FIG. 31

GAIT MODIFICATION APPARATUSES, SYSTEMS AND METHODS

CROSS-REFERENCE TO RELATED APPLICATION

This application claims priority benefit from International Application No. PCT/US2019/057767 filed on Oct. 24, 2019, entitled "Gait Modification Apparatus, Systems and Methods", which claims priority benefit of U.S. Provisional Patent Application No. 62/750,482, filed on Oct. 25, 2018, and entitled "Gait Modification Apparatus, Systems and Methods" each of which is incorporated herein by reference in its entirety.

TECHNICAL FIELD

The present disclosure generally relates to apparatus, systems and methods of gait modification to treat a functional disability and/or pain. More specifically, the present disclosure also relates apparatus, shoe systems and methods of effectuating gait modification by perturbing and biomechanically adjusting the interface of a patient's foot or feet to the ground. The present disclosure also relates to gait monitoring systems that improve compliance and record nature of use information of gait modification apparatus and shoe systems to manage and adjust a gait adjustment prescription over time.

BACKGROUND

A person's gait is their manner of ambulation or locomotion, involving their total body. Gait speed determines the contribution of each participating body segment. Normal walking speed primarily involves the lower extremities, with the arms and trunk providing stability and balance. The faster the speed, the more the body depends on the upper extremities and trunk for propulsion as well as balance and stability. The legs continue to do the most work as the joints produce greater ranges of motion through greater muscle responses. In the bipedal system, the three major joints of the lower body and pelvis work with each other as muscles and momentum move the body forward. The degree to which the body's center of gravity moves during forward movement defines efficiency. The body's center moves both side to side and up and down during gait.

The gait cycle is a repetitive pattern involving steps and strides. A step is one single step, while a stride is a whole gait cycle. Step time is the time from one foot hitting the floor to the other foot hitting the floor. Step width can be described as the mediolateral space between the two feet.

The sequence that occurs in a typical gait cycle (i.e., walking) may be summarized as registration and activation of the gait command within the central nervous system, transmission of the gait command to the peripheral nervous system, contraction of muscles, generation of several forces, regulation of joint forces and moments across synovial joints and skeletal segments, and generation of ground reaction forces, for example. The gait cycle is often classified into two main phases: the stance phase and the swing phase. The stance phase typically occupies about 60% of the gait cycle, while the swing phase typically occupies only about 40%.

Gait involves a combination of open- and close-chain activities. As shown in FIG. 1, a typical gait cycle comprising two steps is also often classified into six detailed phases: 1) heel strike; 2) foot flat; 3) mid-stance; 4) heel-off; 5) toe-off; and 6) mid-swing. A subsequent gait cycle of a walking person repeats the phases beginning with the next heel strike at the end of the mid-swing phase. As also shown in FIG. 1, a common alternative classification of gait breaks the cycle into eight phases: 1) initial contact; 2) loading response; 3) midstance; 4) terminal stance; 5) pre-swing; 6) initial swing; 7) mid-swing; and 8) late swing Abnormal gait is when a person is unable to walk in the usual way. Many systems of the body, such as strength, coordination, and sensation, work together to allow a person to walk with the "normal" or "typical" gait described above. When one or more of these interacting systems is not working properly or typically, it can result in abnormal gait or a walking abnormality. This may be due to injuries, underlying conditions, or problems with the legs and/or feet. For example, congenital deficit, injury or illness involving one or more lower extremities or the spine or torso can result in the advent of a gait irregularity or abnormality. Anatomically, an irregularity can be the result of injury, atrophy, denervation or impaired innervation of one or more muscles or muscle groups, ligament or tendon injury, joint injury or disease, or pain or stiffness of any kind involving the lower extremities, spine or lower torso, for example.

Generally, an irregularity is the manifestation of an asymmetry in the movement or step pattern of the right and left legs. A gait irregularity can include a step duration, step force, or step form difference between the left leg step and the right leg step, for example. An irregularity in the step duration, step force, or step form is commonly referred to as a limp.

Elimination or reduction of gait irregularity is often an important part of a therapeutic and/or healing process, such as to treat a functional disability or pain due to arthritis in the lower limb or lower back pain. It also may be essential to prevent further injury and/or chronic pain, which can be caused by the abnormal stress placed on the body by a gait irregularity. Still further, temporarily or permanently altering a gait (whether it be an irregular gait or a typical gait) can ease pain or discomfort, and potentially establish a new "comfortable" gait or strengthen muscle to prevent or ease the pain or discomfort during a natural gait. As another example, alteration of one's gait can be used as a neuromuscular training aid post joint replacement for faster and more effective rehabilitation.

A number of devices are disclosed in the art for gait alteration or therapy, such as shoe inserts, unstable and shaped shoe soles, variable stiffness soles, knee braces and biomechanical shoe-like devices with floor facing bulbous pods in the forefoot and hindfoot. However, many of these existing technologies are not compatible with everyday life use by being restrictive and cosmetically unappealing. Many existing gait modification technologies also have a relatively limited mechanical effect, and have no mechanism for tracking the compliance and performance of the patient to allow individualized management of a prescription or treatment plan or sequence.

While certain aspects of conventional technologies have been discussed to facilitate disclosure of Applicant's inventions, the Applicant in no way disclaims these technical aspects, and it is contemplated that their inventions may encompass one or more conventional technical aspects.

In this specification, where a document, act or item of knowledge is referred to or discussed, this reference or discussion is not an admission that the document, act or item of knowledge or any combination thereof was, at the priority date, publicly available, known to the public, part of common general knowledge, or otherwise constitutes prior art under the applicable statutory provisions; or is known to be relevant to an attempt to solve any problem with which this specification is concerned.

SUMMARY

Briefly, the present disclosure satisfies the need for gait modification or treatment apparatus, systems and methods that are compatible with use in everyday life (e.g., nonrestrictive and cosmetically appealing at least compared to many prior gait modification treatments). In various embodiments, the present disclosure provides gait modification or treatment apparatus, systems and methods that have a significant mechanical effect tailored to a specific patient's need, and embodiments that provide a mechanism for tracking the compliance and performance of the patient to allow for individualized management of a gait modification prescription or treatment plan or sequence.

The gait modification or treatment apparatus, systems and methods of the present disclosure may be utilized by a user or patient (the terms "user" and "patient" are used synonymously herein) for any reason. For example, the gait modification or treatment apparatus, systems and methods of the present disclosure may be utilized to treat a functional disability and/or pain (such as, but not limited to, pain and/or arthritis in a lower limb (e.g., knee osteoarthritis) and/or back pain), and thereby enhance the quality of life of the user. As yet another example, the gait modification or treatment apparatus, systems and methods of the present disclosure may be utilized as a neuro-muscular training aid, such as post-joint replacement for a relatively faster and more effective rehabilitation.

Generally, the gait modification or treatment apparatus, systems and methods of the present disclosure may provide the above-noted treatments or functions by modifying a user's gait and providing instability during the gait by perturbing and/or biomechanically adjusting the interface of at least one foot of the user and the ground. The gait modification or treatment apparatus, systems and methods thereby form an unstable shoe apparatus or system to particularly or purposefully modify the gait of the user in at least one way or metric.

In some embodiments, the gait modification or treatment apparatus, systems and methods advantageously make use of at least one rectilinear or planar facetted projection that forms a first planar guide surface for at least partial contact or engagement with the ground during at least the foot flat and mid-stance phases of a gait. The at least one rectilinear or planar facetted projection may also provide at least one second planar guide surface for at least partial engagement with the ground during the heal strike phase, and at least one third planar guide surface for at least partial engagement with the ground during the heel-off phase. The relative configuration (e.g., size, shape, position and/or orientation) between the first planar guide surface and the at least one second guide planar surface may be effective in directing transition there-between during one or more phases of the gait. Similarly, the relative configuration (e.g., size, shape, position and/or orientation) between the first planar guide surface and the at least one third planar guide surface may be effective in directing transition there-between during one or more phases of the gait. The at least one projection may include additional planar and/or non-planar (e.g., arcuate) guide surfaces. The guide surfaces of the at least one projection may provide a substantial amount of foot and ground reaction force control. Also, the at least one projection may be compatible with daily use (e.g., the at least one projection may be non-restrictive and/or not cosmetically obtrusive at least compared to many prior gait modification treatments).

The gait modification or treatment apparatus, systems and methods of the present disclosure may also provide the above-noted treatments or functions by employing a monitoring system or method that tracks the use/activities of the gait modification/treatment apparatus or systems (and thereby the patient themselves) to improve compliance and record the nature of use to manage and adjust an individual's particularly provided/selected unstable foot-ground interface over time to enhance the effectiveness of the treatment. The monitoring system or method may thereby allow individualized management of a sequence of incremental prescriptive changes via differing gait modification or treatment apparatus, systems and methods of the present disclosure.

In one aspect, the present disclosure provides a gait modification apparatus comprising a posterior projection extending from an underside of a shoe in a hindfoot region thereof, the posterior projection defining a posterior planar ground engagement surface and a plurality of posterior planar guide surfaces extending outwardly and dorsally from portions of the periphery of the posterior ground engagement surface at respective angles. The gait modification apparatus further comprises an anterior projection extending from the underside of a shoe in a forefoot region thereof, the anterior projection defining an anterior planar ground engagement surface and a plurality of anterior planar guide surfaces extending outwardly and dorsally from portions of the periphery of the anterior ground engagement surface at respective angles.

In some embodiments, the plurality of posterior planar guide surfaces extend from the entirety of the periphery of the posterior planar ground engagement surface. In some embodiments, the plurality of posterior planar guide surfaces comprises at least four planar surfaces. In some embodiments, the plurality of posterior planar guide surfaces comprises at least six planar surfaces.

In some embodiments, the plurality of posterior planar guide surfaces comprises at least one hind planar surface that extends dorsally and posteriorly from a posterior side portion of the periphery of the posterior planar engagement surface. In some such embodiments, the plurality of posterior planar guide surfaces comprises at least one fore planar surface that extends dorsally and anteriorly from an anterior side portion of the periphery of the posterior planar engagement surface. In some such embodiments, the plurality of posterior planar guide surfaces comprises at least one medial planar surface that extends dorsally and medially from a medial side portion of the periphery of the posterior planar engagement surface, and at least one lateral planar surface that extends dorsally and lateral from a lateral side portion of the periphery of the posterior planar engagement surface.

In some embodiments, the posterior planar ground engagement surface is angled along the dorsal-planar direction as it extends along the medial-lateral direction.

In some embodiments, the posterior planar ground engagement surface is oriented normal to the dorsal-planar direction.

In some embodiments, the plurality of anterior planar guide surfaces extend from the entirety of the periphery of the anterior planar ground engagement surface. In some embodiments, the plurality of anterior planar guide surfaces comprises at least four planar surfaces. In some embodiments, the plurality of anterior planar guide surfaces comprises at least six planar surfaces.

In some embodiments, the plurality of anterior planar guide surfaces comprises at least one hind planar surface that extends dorsally and posteriorly from a posterior side portion of the periphery of the anterior planar engagement surface. In some such embodiments, the plurality of anterior planar guide surfaces comprises at least one fore planar surface that extends dorsally and anteriorly from an anterior side portion of the periphery of the anterior planar engagement surface. In some such embodiments, the plurality of anterior planar guide surfaces comprises at least one medial planar surface that extends dorsally and medially from a medial side portion of the periphery of the anterior planar engagement surface, and at least one lateral planar surface that extends dorsally and lateral from a lateral side portion of the periphery of the anterior planar engagement surface.

In some embodiments, the anterior planar ground engagement surface is angled along the dorsal-planar direction as it extends along the medial-lateral direction. In some embodiments, the anterior planar ground engagement surface is oriented normal to the dorsal-planar direction.

In some embodiments, the plurality of posterior planar guide surfaces extend from the entirety of the periphery of the posterior planar ground engagement surface, and wherein the plurality of anterior planar guide surfaces extend from the entirety of the periphery of the anterior planar ground engagement surface. In some such embodiments, the plurality of anterior planar guide surfaces comprises at least six planar surfaces, and wherein the plurality of posterior planar guide surfaces comprises at least six planar surfaces. In some other such embodiments, the plurality of anterior planar guide surfaces comprises at least four planar surfaces, and wherein the plurality of posterior planar guide surfaces comprises at least four planar surfaces. In some other such embodiments, the plurality of anterior planar guide surfaces comprises at least one hind planar surface that extends dorsally and posteriorly from a posterior side portion of the periphery of the anterior planar engagement surface, at least one fore planar surface that extends dorsally and anteriorly from an anterior side portion of the periphery of the anterior planar engagement surface, at least one medial planar surface that extends dorsally and medially from a medial side portion of the periphery of the anterior planar engagement surface, and at least one lateral planar surface that extends dorsally and lateral from a lateral side portion of the periphery of the anterior planar engagement surface, and wherein the plurality of posterior planar guide surfaces comprises at least one hind planar surface that extends dorsally and posteriorly from a posterior side portion of the periphery of the posterior planar engagement surface, at least one fore planar surface that extends dorsally and anteriorly from an anterior side portion of the periphery of the posterior planar engagement surface, at least one medial planar surface that extends dorsally and medially from a medial side portion of the periphery of the posterior planar engagement surface, and at least one lateral planar surface that extends dorsally and lateral from a lateral side portion of the periphery of the posterior planar engagement surface.

In some embodiments, the posterior projection and the anterior projection are removably coupled to the underside of the shoe. In some embodiments, the posterior projection and the anterior projection are fixedly coupled to or integral with the underside of the shoe. In some embodiments, the posterior projection and the anterior projection are spaced from each other. In some embodiments, the posterior projection and the anterior projection abut each other. In some embodiments, the posterior projection and the anterior projection are formed of multicork, ethylene vinyl acetate, styrene butadiene rubber or a combination thereof.

In some embodiments, the posterior projection and the anterior projection define a maximum thickness along the dorsal-planar direction between the underside of the shoe and the posterior planar ground engagement surface and the anterior planar ground engagement surface, respectively, within the range of about 1 cm to about 3 cm.

In another aspect, the present disclosure provides a gait modification system comprising a gait modification apparatus as described above, and at least one sensor configured to monitor physical activity of a patient utilizing the gait modification apparatus to determine a gait modification prescription plan. In some embodiments, the at least one sensor is configured to monitor at least one aspect of a gait of the patient.

In another aspect, the present disclosure provides a method of modifying a gait of a patient. The method comprises coupling a first posterior projection to an underside of a left-footed shoe in a hindfoot region thereof, the first posterior projection defining a posterior planar ground engagement surface and a plurality of posterior planar guide surfaces extending outwardly and dorsally from portions of the periphery of the posterior ground engagement surface at respective angles, and coupling a first anterior projection to the underside of the left-footed shoe in a forefoot region thereof, the first anterior projection defining an anterior planar ground engagement surface and a plurality of anterior planar guide surfaces extending outwardly and dorsally from portions of the periphery of the anterior ground engagement surface at respective angles. The method further comprises coupling a second posterior projection to an underside of a right-footed shoe in a hindfoot region thereof, the second posterior projection defining a posterior planar ground engagement surface and a plurality of posterior planar guide surfaces extending outwardly and dorsally from portions of the periphery of the posterior ground engagement surface at respective angles, and coupling a second anterior projection to the underside of the right-footed shoe in a forefoot region thereof, the second anterior projection defining an anterior planar ground engagement surface and a plurality of anterior planar guide surfaces extending outwardly and dorsally from portions of the periphery of the anterior ground engagement surface at respective angles.

In some embodiments, the method further comprises associating at least one sensor with the patient, wherein the sensor is configured to monitor physical activity of the patient. In some embodiments, the at least one sensor is configured to monitor at least one aspect of a gait of the patient. In some embodiments, the method further comprises determining a gait modification prescription plan of differing gait modification apparatuses based on the monitored activity of the patient. In some such embodiments, the method further comprises replacing or modifying at least one of the first posterior projection, the first anterior projection, the second posterior projection and the second anterior projection according to the determined gait modification prescription plan.

In another aspect, the present disclosure provides a gait modification apparatus comprising a sculpted sole for use on the underside of a shoe comprising a projection. The projection comprises a planar ground engagement surface that extends from the hindfoot to the forefoot, a posterior and medial relief surface extending dorsally from a posterior and anterior edge of the ground engagement surface toward the periphery of the sole, a planar lateral relief surface extending anteriorly and laterally from an anterior edge of the ground engagement surface toward the periphery of the sole, and a planar anterior relief surface extending anteriorly and medially from an anterior edge of the ground engagement surface toward the periphery of the sole.

In another aspect, the present disclosure provides a gait modification apparatus comprising a projection for use on the underside of a shoe comprising that defines a planar ground engagement surface. The projection extends from the hindfoot to the forefoot, and the planar ground engagement surface defines a bulbous posterior end portion in the hindfoot and a bulbous anterior end portion in the forefoot.

In another aspect, the present disclosure provides a gait modification apparatus comprising a sole for use on the underside of a shoe comprising, and a narrow elongate rail member that extends from the hindfoot to the forefoot, the rail member defining a narrow elongate ground engagement surface.

In another aspect, the present disclosure provides a gait modification apparatus comprising a sole for use on the underside of a shoe comprising, and an array of a plurality of variably compressive pegs extending from the sole, the pegs defining a ground engagement surface. The array of pegs extends at least in the hindfoot and the forefoot portions of the sole.

In another aspect, the present disclosure provides a gait modification system comprising a gait modification apparatus as described above, and at least one sensor configured to monitor physical activity of a patient utilizing the gait modification apparatus to determine a gait modification prescription plan.

In another aspect, the present disclosure provides a method of modifying a gait of a patient comprising coupling a gait modification apparatus as described above to the underside of a shoe of the patient.

In some embodiments, the method further comprises associating at least one sensor with the patient, wherein the sensor is configured to monitor physical activity of the patient. In some embodiments, the method further comprises determining a gait modification prescription plan of differing gait modification apparatuses based on the monitored activity of the patient. In some such embodiments, the method further comprises replacing or modifying the gait modification apparatus according to the determined gait modification prescription plan.

The gait modification or treatment apparatus, systems and methods of the present disclosure may address one or more of the problems and deficiencies of the art discussed above. However, it is contemplated that the gait modification or treatment apparatus, systems and methods of the present disclosure may prove useful in addressing other problems and deficiencies in a number of technical areas. Therefore, the disclosed and claimed inventions should not necessarily be construed as limited to addressing any of the particular problems or deficiencies discussed herein.

Certain embodiments of the presently-disclosed gait modification or treatment apparatus, systems and methods have several features, no single one of which is solely responsible for their desirable attributes. Without limiting the scope of the gait modification or treatment apparatus, systems and methods of the present disclosure (e.g., those that are defined by the claims that follow), their more prominent features will now be discussed briefly. After considering this discussion, and particularly after reading the section of this specification entitled "Detailed Description," one will understand how the features of the various embodiments disclosed herein provide a number of advantages over the current state of the art.

These and other features and advantages of this disclosure will become apparent from the following detailed description of the various aspects of the disclosure taken in conjunction with the appended claims and the accompanying drawings.

BRIEF DESCRIPTION OF THE DRAWINGS

The present disclosure will hereinafter be described in conjunction with the following drawing figures, which are not necessarily drawn to scale for ease of understanding, wherein the same reference numerals retain their designation and meaning for the same or like elements throughout the various drawings, and wherein:

FIG. 29 illustrates a side view of an exemplary gait modification/treatment apparatus, system and method according the present disclosure comprising a shoe sole with an exemplary array of variable stiffness pegs;

FIG. 30 illustrates a back view of the shoe sole of FIG. 29;

FIG. 31 illustrates a bottom view of the shoe sole of FIG. 29;

DETAILED DESCRIPTION

Aspects of the present disclosure and certain features, advantages, and details thereof, are explained more fully below with reference to the non-limiting embodiments illustrated in the accompanying drawings. Descriptions of well-known materials, fabrication tools, processing techniques, etc., are omitted so as to not unnecessarily obscure the inventions in detail. It should be understood, however, that the detailed description and the specific example(s), while indicating embodiments of inventions, are given by way of illustration only, and are not by way of limitation. Various substitutions, modifications, additions and/or arrangements within the spirit and/or scope of the underlying inventive concepts will be apparent to those skilled in the art from this disclosure.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant nearest the torso, while "distal"

indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. In addition, for the purposes of this disclosure, the term "posterior" means a direction towards the heel of a foot, and the term "anterior" means direction towards the tips of toes of a foot. When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Any examples of parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

Figure 2:
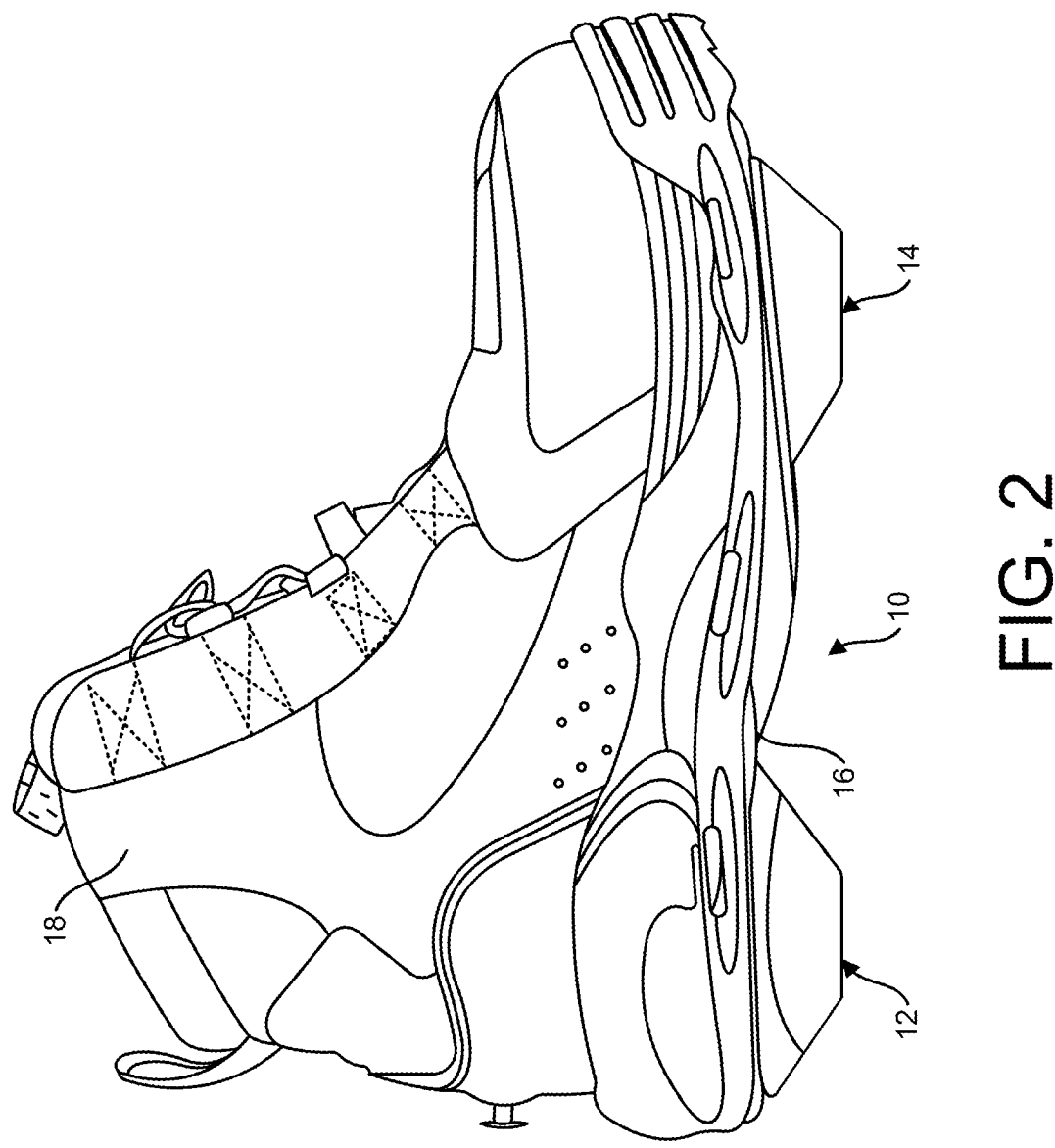
FIG. 2 illustrates a side view of a shoe including an exemplary gait modification/treatment apparatus, system and method according the present disclosure comprising exemplary rectilinear projections in the hindfoot and the forefoot.
Figure 3:
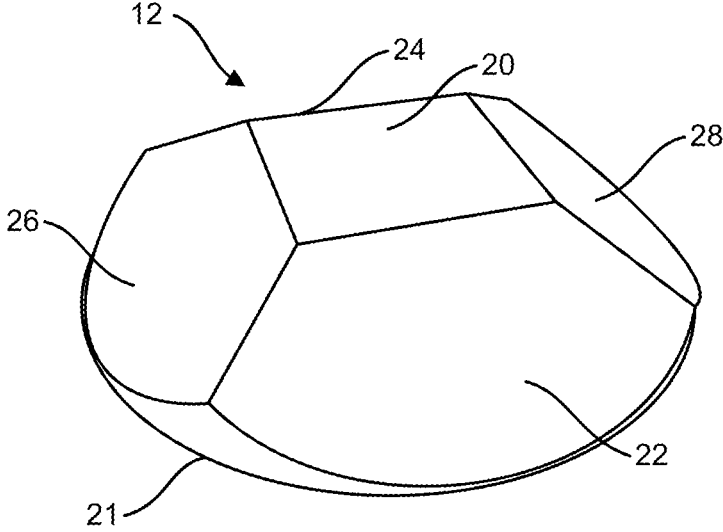
FIG. 3 illustrates an elevational perspective view of the hindfoot rectilinear projection of FIG. 2.
Figure 4:
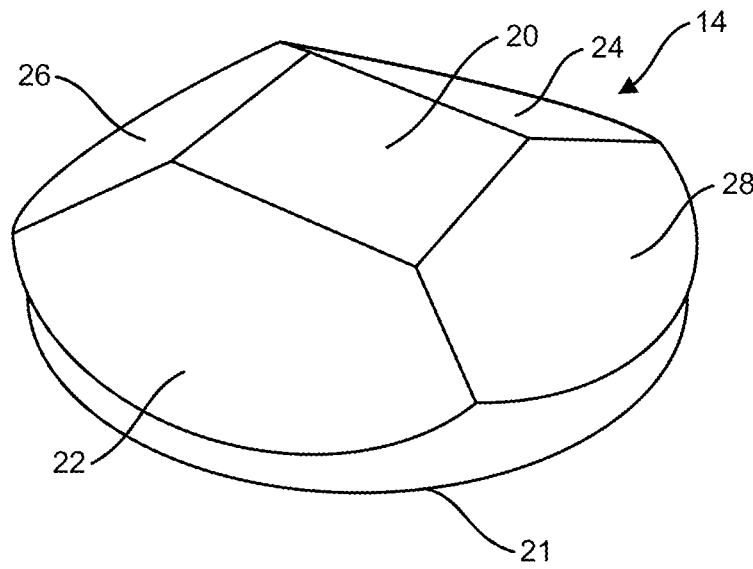
FIG. 4 illustrates an elevational perspective view of the forefoot rectilinear projection of FIG. 2.

Referring to the drawings, and with particular reference to FIGS. 2-4, there is illustrated an exemplary gait modification/treatment device, apparatus, system and/or method 10 that modifies the gait of a user or person by guiding the respective foot of the user to control the trajectory, center of pressure, direction of ground reaction forces, level of instability and/or orientation of the foot during gait (and/or other static and/or dynamic loading situations). Although modification of one foot or shoe of a user may be illustrated or described herein, it is hereby contemplated that modification of the other foot or shoe may or may not be modified, such as modified specific to the phase(s) of the gait cycle pertaining to that foot/shoe.

Figure 1:
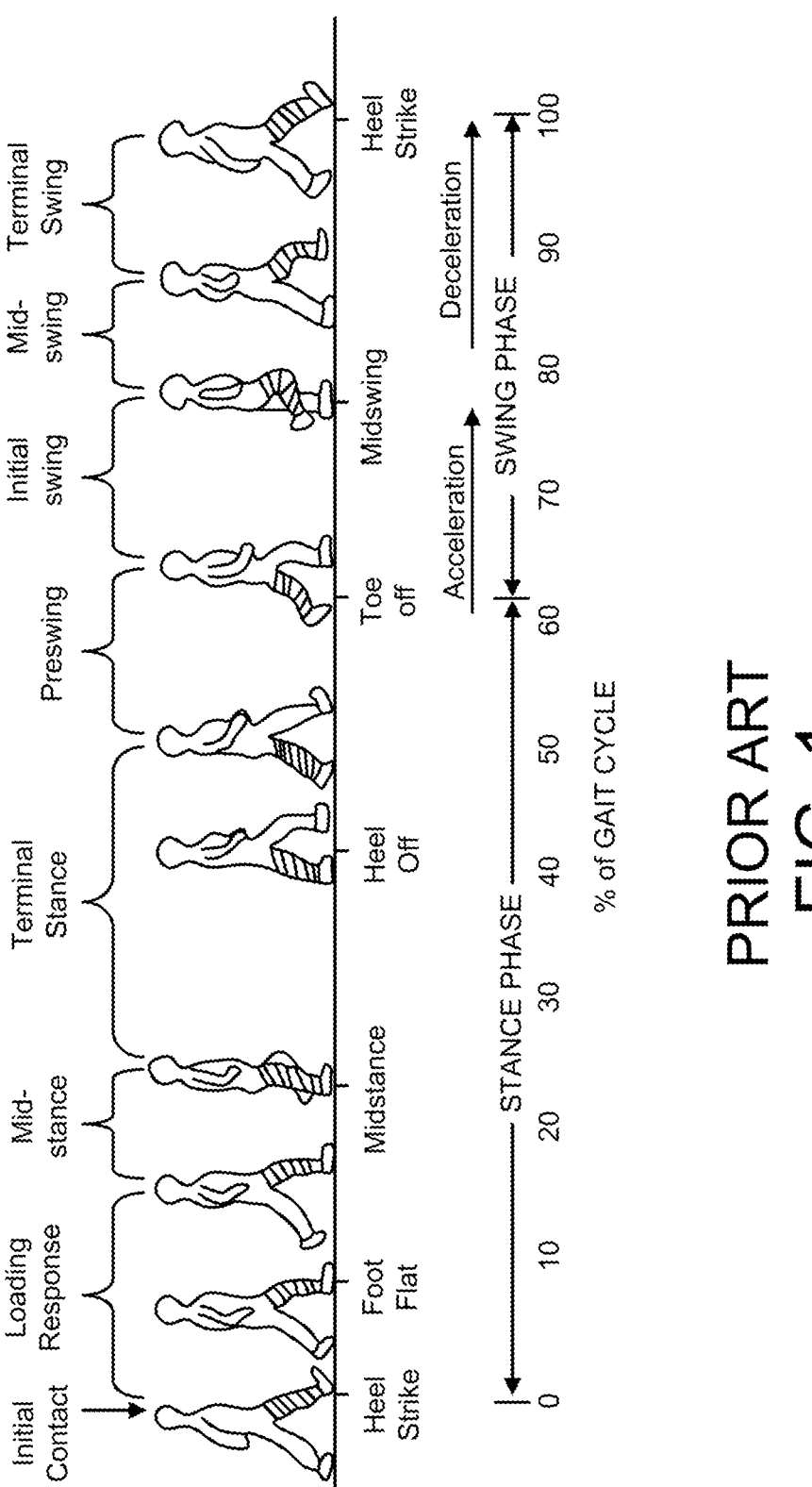
FIG. 1 is a schematic illustrating a typical gait cycle for a person and phases thereof.

As shown in FIGS. 2-4, the gait modification/treatment device, apparatus, system and/or method 10 comprises the use of a hindfoot projection 12 and a forefoot projection 14 to guide foot trajectory and inclination, control the direction of ground reaction forces, and provide instability during gait. Each of the hindfoot projection 12 and the forefoot projection 14 is configured to extend from the plantar or bottom surface 16 of a shoe 18, as shown in FIG. 1. The hindfoot and forefoot projections 12, 14 may be separate and distinct components, or be coupled together or portions of a unitary component. The hindfoot projection 12 may be positioned at least generally or partially at the hindfoot portion of a shoe 18, and the forefoot projection 14 may be positioned at least generally or partially at the forefoot portion of a shoe 18. The particular positions of the hindfoot and forefoot projections 12, 14 on a shoe 18 can be selected to control or configure the centers of pressure, and the origin and direction of the ground reaction forces, during a gait cycle.

The hindfoot and forefoot projections 12, 14 may be configured to be fixed to the underside/plantar side 16 of a shoe 18, or may be configured to removably attach to the underside 16 of a shoe 18 (e.g., as an overlay), as shown in FIG. 1. When configured to be removably coupled to a corresponding shoe 18, the hindfoot and forefoot projections 12, 14 may be repositionable such that various positions and orientations of the hindfoot and forefoot projections 12, 14 on the underside 16 of the shoe 18 can be selected and/or modified. Further, differently configured or designed hindfoot and forefoot projections 12, 14 can be used (i.e., the hindfoot and forefoot projections 12, 14 can be swapped out and change over time). In some embodiments, the hindfoot projection 12 and/or the forefoot projection 14 may be removably coupled to the underside 16 of a shoe 18 via hook and loop fasteners or other mechanical adjustable fasteners. In some other embodiments, the hindfoot projection 12 and/or the forefoot projection 14 may be fixedly coupled to the underside 16 of a shoe 18 via an adhesive or a permanent mechanical fastener. In still another embodiment, the hindfoot projection 12 and/or the forefoot projection 14 may be co-molded or otherwise formed as part of the underside 16 of a shoe 18.

The hindfoot and forefoot projections 12, 14 may be made of any material such that they substantially retain their shape while being walked on during the gait cycle of a user. In some embodiments, the hindfoot projection 12 and/or the forefoot projection 14 may be formed of a material that is appropriate for a projection that is walked on over a relatively long period of time. In some embodiments, the hindfoot projection 12 and/or the forefoot projection 14 may be formed of a material that is typically or conventionally used in orthotics and/or shoe soles. For example, the hindfoot projection 12 and/or the forefoot projection 14 may be formed of multicork, ethylene vinyl acetate (EVA) and/or styrene butadiene rubber (SBR, Buna-S), such as a material with a durometer within the range of about 35 Shore A to about 80 Shore A (e.g., a durometer of about 50 Shore A or about 55 Shore A).

The maximum thickness of the hindfoot and forefoot projections 12, 14 measured in the dorsal-plantar direction from the underside 16 of a shoe 18 from which the respective projections 12, 14 extend may be within the range of about 1 cm to about 3 cm. The maximum width of the hindfoot and forefoot projections 12, 14 (such as at the interface with the underside 16 of a shoe 18) measured in the medial-lateral direction, and/or the maximum length of the hindfoot and forefoot projections 12, 14 (such as at the interface with the underside 16 of a shoe 18) measured in the posterior-anterior direction, may be within the range of about 5 cm to about 12 cm. The maximum width and/or length of the hindfoot projection 12 and/or the forefoot projection 14 may be greater than or smaller than the respective portions of the underside 16 of the shoe 18 from which they extend. The dimensions of the hindfoot and forefoot projections 12, 14 may vary, such as with the size of a particular patient (e.g., a particular shoe 18) for example. The thickness, width, length or other dimensions and/or configuration of the hindfoot projection 12 may differ from the forefoot projection 14, or the hindfoot projection 12 may identical to the forefoot projection 14.

As shown in FIGS. 3 and 4, both the hindfoot and forefoot projections 12, 14 may include or define a planar ground engagement surface 20. The planar ground engagement surface 20 may be the surface that is positioned or extends furthest in the plantar direction from the underside 16 of a shoe 18. The engagement surface 20 may at least partially contact or engage with a ground surface during at least the foot flat and/or mid-stance phases of a gait cycle. In some embodiments, the maximum width and/or length of the engagement surface 20 may be within the range of about 2 cm to about 8 cm. The surface area of the engagement surface 20 hindfoot and/or forefoot projections 12, 14 may be smaller than the surface area of the dorsal surface or portion 21 that interfaces with the underside 16 of the shoe 18.

The engagement surface 20 of the hindfoot and forefoot projections 12, 14 may be of any shape, size and orientation with respect to the dorsal surface or portion 21 that interfaces with the underside 16 of the shoe 18 (and thereby with respect to the underside 16 of the shoe 18 itself), and may differ from each other (or be identical). For example, the engagement surface 20 of the hindfoot projection 12 and/or the forefoot projection 14 may be angled (e.g., with respect to the dorsal surface or portion 21 and the respective portion of the underside 16 of the shoe 18) in the dorsal or plantar direction as it extends along the posterior-anterior direction, and/or may be angled in the dorsal or plantar direction as it extends along the medial-lateral direction, as shown in FIGS. 2-4.

As shown in FIGS. 3 and 4, hindfoot and forefoot projections 12, 14 may be facetted such that a plurality of planar guide or relief (and/or curved or arcuate) surfaces extend from the engagement surface 20 toward the dorsal surface or portion 21 (i.e., the underside 16 of a shoe 18) at an angle (i.e., are angled dorsally). The engagement surface 20 and the guide surfaces of the hindfoot and forefoot projections 12, 14 may provide a substantial amount of foot and ground reaction force control, and dictate or provide for the trajectory of the respective foot, and/or instability during the gait cycle.

For example, as shown in FIGS. 3 and 4, the hindfoot projection 12 and/or the forefoot projection 14 may include at least one generally hind- or posteriorly-facing relief guide surface 22 (hereinafter "hind guide surface 22") that extends dorsally and posteriorly from the engagement surface 20 at a particular angle. The at least one hind guide surface 22 of the hindfoot and forefoot projections 12, 14 may thereby form the posterior edge(s) of the engagement surface 20. The at least one hind surfaces 22 may or may not be angled along the posterior-anterior direction across its medial-lateral width. The at least one hind guide surface 22 of the hindfoot projection 12 may at least partially engage with the ground during the heal strike phase of a user's gait. The relative configuration (e.g., size, shape, position and/or orientation) between the engagement surface 20 and the at least one hind guide surface 22 may be effective in directing transition there-between during one or more phases of the gait cycle. The at least one hind guide surface 22 may determine trajectory of the respective foot, determine the direction of ground reaction forces and/or provide instability during at least a portion of one or more phase of a gait cycle. The at least one hind guide surface 22 of the hindfoot projection 12 and the forefoot projection 14 may differ or be identical.

As also shown in FIGS. 3 and 4, the hindfoot projection 12 and/or the forefoot projection 14 may also include at least one generally fore- or anteriorly-facing relief or guide surface 24 (hereinafter "fore guide surface 24") that extends dorsally and anteriorly from the engagement surface 20 at a particular angle. The at least one fore guide surface 24 of the hindfoot and forefoot projections 12, 14 may thereby form the anterior edge(s) of the engagement surface 20. The at least one fore guide surfaces 24 may or may not be angled along the posterior-anterior direction across its medial-lateral width. The at least one fore guide surface 24 of the forefoot projection 14 may at least partially engage with the ground during the toe-off phase of a user's gait. The relative configuration (e.g., size, shape, position and/or orientation) between the engagement surface 20 and the at least one fore guide surface 24 may be effective in directing transition there-between during one or more phases of the gait cycle. The at least one fore guide surface 24 may determine trajectory of the respective foot, determine the direction of ground reaction forces and/or provide instability during at least a portion of one or more phase of a gait cycle. The at least one fore guide surface 24 of the hindfoot projection 12 and the forefoot projection 14 may differ or be identical.

As also shown in FIGS. 3 and 4, the hindfoot projection 12 and/or the forefoot projection 14 may further include at least one generally medially-facing relief or guide surface 26 (hereinafter "medial guide surface 26") that extends dorsally and medially from the engagement surface 20 at a particular angle. The at least one medial guide surfaces 26 may or may not be angled along the medial-lateral direction across its posterior-anterior length. The at least one medial guide surface 26 of the hindfoot and forefoot projections 12, 14 may thereby form the medial edge(s) of the engagement surface 20. The relative configuration (e.g., size, shape, position and/or orientation) between the engagement surface 20 and the at least one medial guide surface 26 may be effective in directing transition there-between during one or more phases of the gait cycle. The at least one medial guide surface 26 may determine trajectory of the respective foot, determine the direction of ground reaction forces and/or provide instability during at least a portion of one or more phase of a gait cycle. The at least one medial guide surface 26 of the hindfoot projection 12 and the forefoot projection 14 may differ or be identical.

As also shown in FIGS. 3 and 4, the hindfoot projection 12 and/or the forefoot projection 14 may include at least one generally laterally-facing relief or guide surface 28 (hereinafter "lateral guide surface 28") that extends dorsally and laterally from the engagement surface 20 at a particular angle. The at least one lateral guide surface 28 may or may not be angled along the medial-lateral direction across its posterior-anterior length. The at least one lateral guide surface 28 of the hindfoot and forefoot projections 12, 14 may thereby form the lateral edge(s) of the engagement surface 20. The relative configuration (e.g., size, shape, position and/or orientation) between the engagement surface 20 and the at least one lateral guide surface 28 may be effective in directing transition there-between during one or more phases of the gait cycle. The at least one lateral guide surface 28 may determine trajectory of the respective foot, determine the direction of ground reaction forces and/or provide instability during at least a portion of one or more phase of a gait cycle. The at least one lateral guide surface 28 of the hindfoot projection 12 and the forefoot projection 14 may differ or be identical.

As noted above, the configuration and relative arrangement (and number) of the guide/relief surfaces and the engagement surface 20 may determine a particular trajectory of a respective foot, determine the direction of ground reaction forces and/or provide a particular instability during at least a portion of one or more phase of a gait cycle. As such, although one hind guide surface 22, one fore guide surface 24, one medial guide surface 26 and one lateral guide surface 28 is shown in the illustrated embodiments of the hindfoot projection 12 and the forefoot projection 14 in FIGS. 3 and 4 such that the engagement surface 20 is a quadrilateral (e.g., a regular or irregular quadrilateral), the hindfoot projection 12 and the forefoot projection 14 may include any number of guide/relief surfaces (e.g., planar relief/guide surfaces) that extend or are angled dorsally therefrom to provide particularly desired trajectory, ground reaction force and/or instability profiles. For example, the side/relief surfaces (e.g., planar relief/guide surfaces) and the engagement surface 20 may be configured and oriented relative to one another to create preferred orientations for the trajectory of the foot during at least a portion of one or more phase of a gait cycle, as well as configuring and orienting the outer peripheral edges of the engagement surface 20 to provide instability during at least a portion of one or more phase of the gait cycle. For example, the hindfoot projection 12 and/or the forefoot projection 14 may be of any facetted geometry (e.g., geometries formed of planar surfaces). For example, the hindfoot projection 12 and/or the forefoot projection 14 may be of a facetted regular geometry or a facetted irregular geometry. The hindfoot projection 12 and/or the forefoot projection 14 may be of a truncated triangular, square, rectangular or trapezoidal pyramidal form with parallel or inclined dorsal 21 and/or engagement 20 surfaces, for example.

Figure 5:
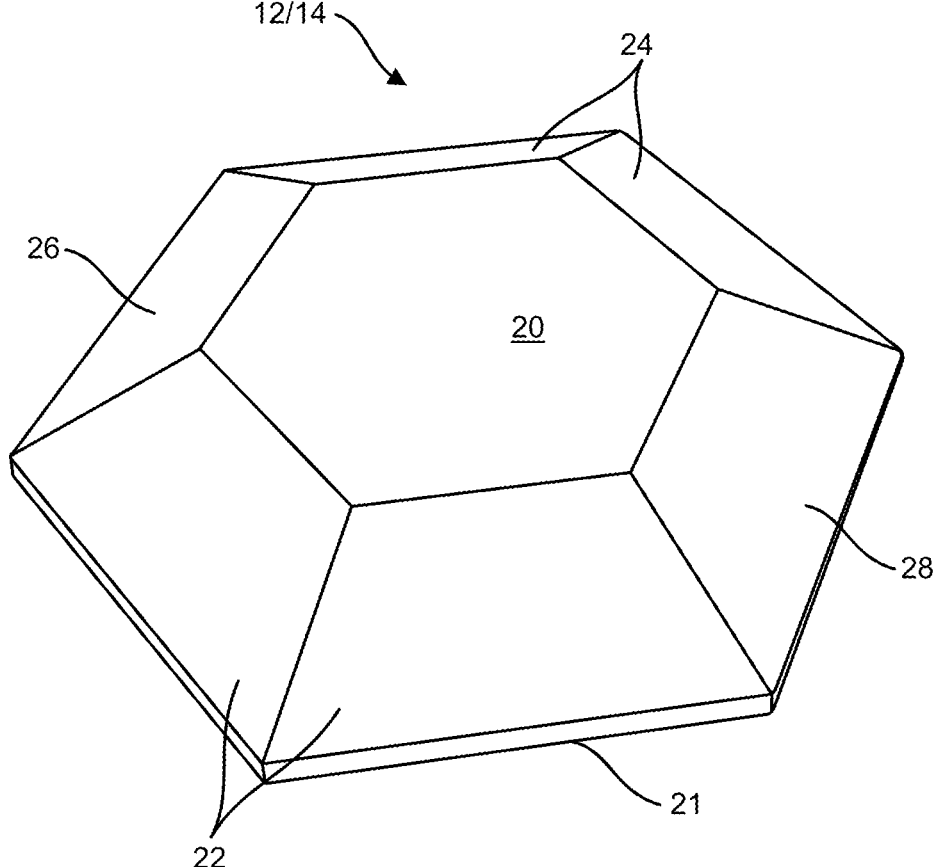
FIG. 5 illustrates an elevational perspective view of another exemplary hindfoot and/or forefoot rectilinear projection of a gait modification/treatment apparatus, system and method according the present disclosure.
Figure 6:
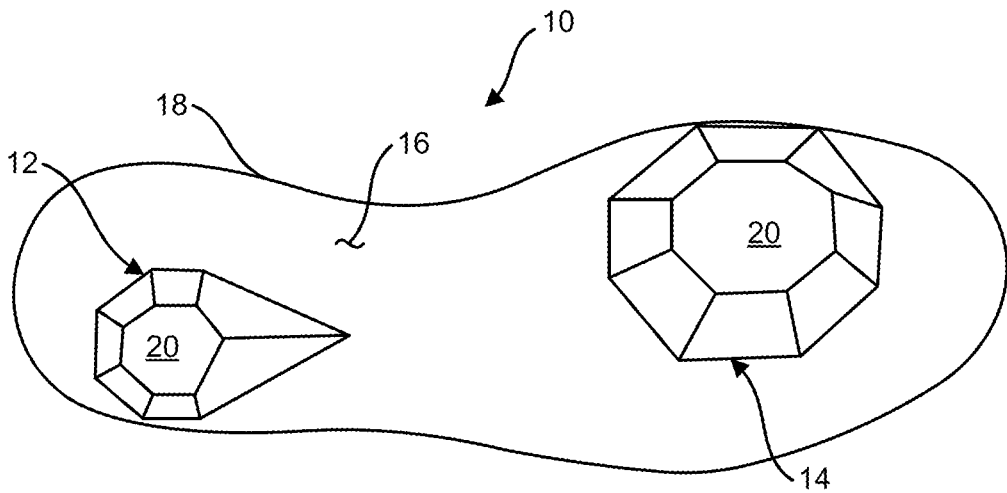
FIG. 6 illustrates a bottom view of a shoe sole including another exemplary gait modification/treatment apparatus, system and method according the present disclosure comprising exemplary rectilinear projections in the hindfoot and the forefoot.
Figure 7:
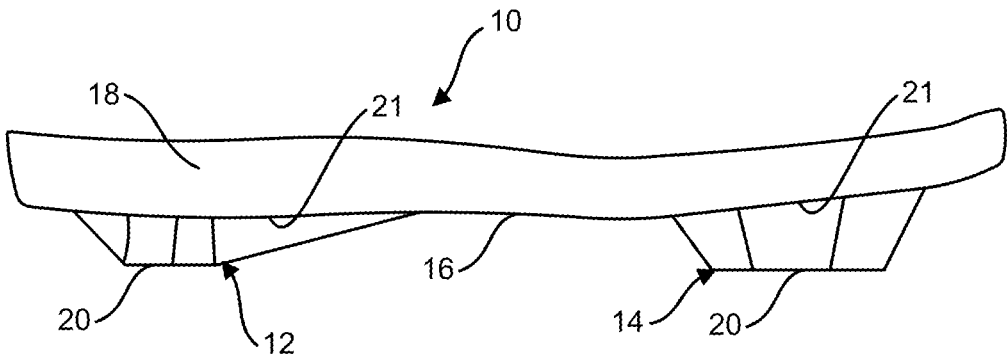
FIG. 7 illustrates a side view of the shoe sole and rectilinear projections of FIG. 6.
Figure 8:
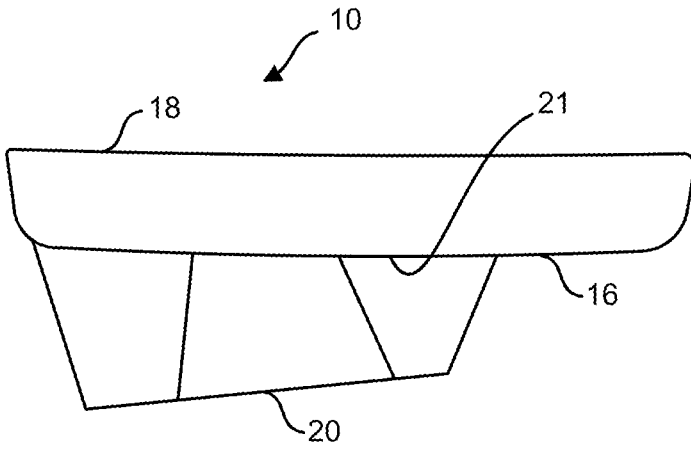
FIG. 8 illustrates a back view of the shoe sole and rectilinear projections of FIG. 6.
Figure 9:
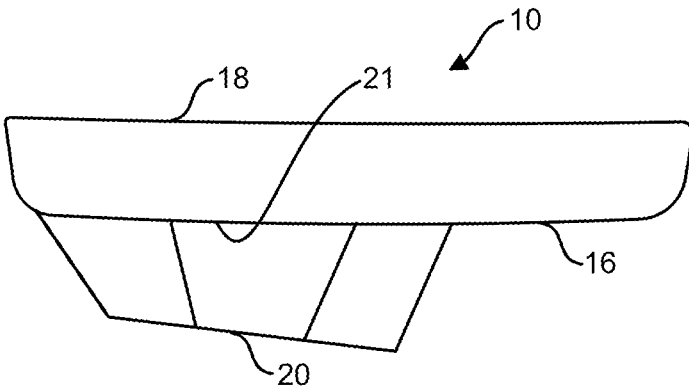
FIG. 9 illustrates a front view of the shoe sole and rectilinear projections of FIG. 6.

In some embodiments, the hindfoot projection 12 and/or the forefoot projection 14 may be configured with six relief/guide surfaces extending from the engagement surface 20 such that the engagement surface is of a regular or irregular hexagonal shape, as shown in FIGS. 5-7. Such hexagonal forms of the hindfoot projection 12 and/or the forefoot projection 14, as shown in FIGS. 5-7 for example, may provide advantageous or desirable levels of instability and trajectory control to effectively modify/treat a person's abnormal gait cycle. For example, as shown in FIG. 5, the hindfoot projection 12 and/or the forefoot projection 14 may include a pair of hind guide surfaces 22, a pair of fore guide surface 24, one medial guide surface 26 and one lateral guide surface 28 each extending from the engagement surface 20.

FIG. 5 illustrates an exemplary hindfoot projection 12 and/or forefoot projection 14 of a regular hexagonal shape, while FIGS. 6 and 7 illustrate an exemplary irregular asymmetric hindfoot projection 12 and an irregular asymmetric octagonal forefoot projection 14. In some embodiments, an asymmetric hindfoot projection 12 and/or forefoot projection 14 may allow for flexibility in locating the respective projection 12, 14 in or along the medial-lateral direction on the underside 16 of a shoe 18 without it extending past or over a medial or lateral peripheral edge of the underside 16 of the shoe 18, as shown with the hindfoot projection 12 in FIG. 6. Hindfoot projections 12 and/or forefoot projections 14 that are asymmetric and elongated (in the medial-lateral or posterior-anterior directions) may provide or form relief/guide surfaces (e.g., at least one hind guide surface 22 and/or at least one fore guide surface 24) that act as relatively large and gradual (e.g., orientated at a relatively shallow angle with respect to the engagement surface 20 thereof) ramp surfaces or edges for smoothly transitioning onto and off the projections 12, 14 (e.g., at heel-strike and toe-off), but also in smoothly transitioning between the hindfoot and forefoot projections 12, 14 within the stance phase of a gait cycle. A particular gait modification or treatment method or plan/prescription including a plurality of differing hindfoot projections 12 and/or forefoot projections 14 may initially utilize such smoothly transitioning asymmetric and elongated projections 12, 14 before utilizing more aggressive projections 12, 14, as shown in the progression of projections 12, 14 extending from right to left in FIG. 11B.

Figure 11A:
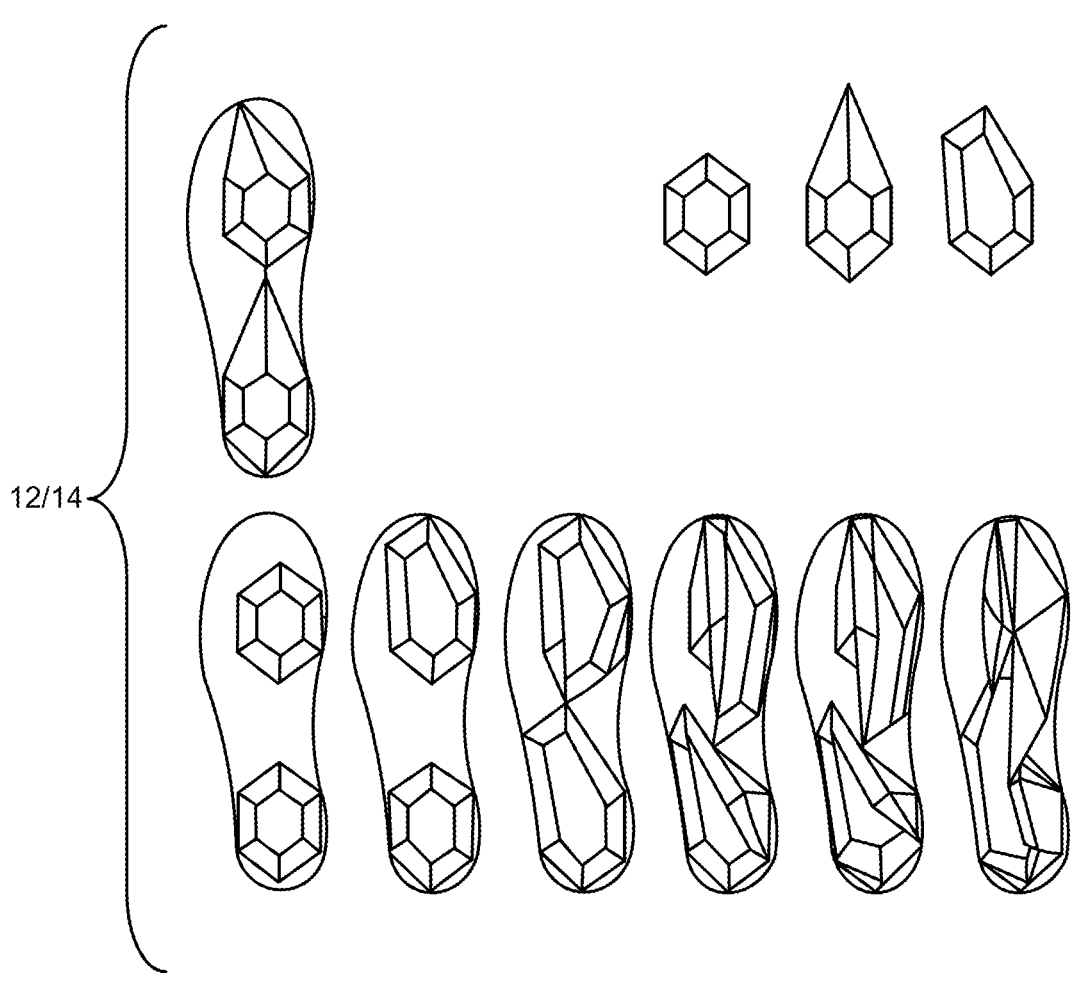
FIG. 11A illustrates a bottom view of a shoe sole including a plurality of differing exemplary gait modification/treatment apparatuses, systems and methods according the present disclosure comprising exemplary rectilinear projections in the hindfoot and the forefoot.
Figure 11B:
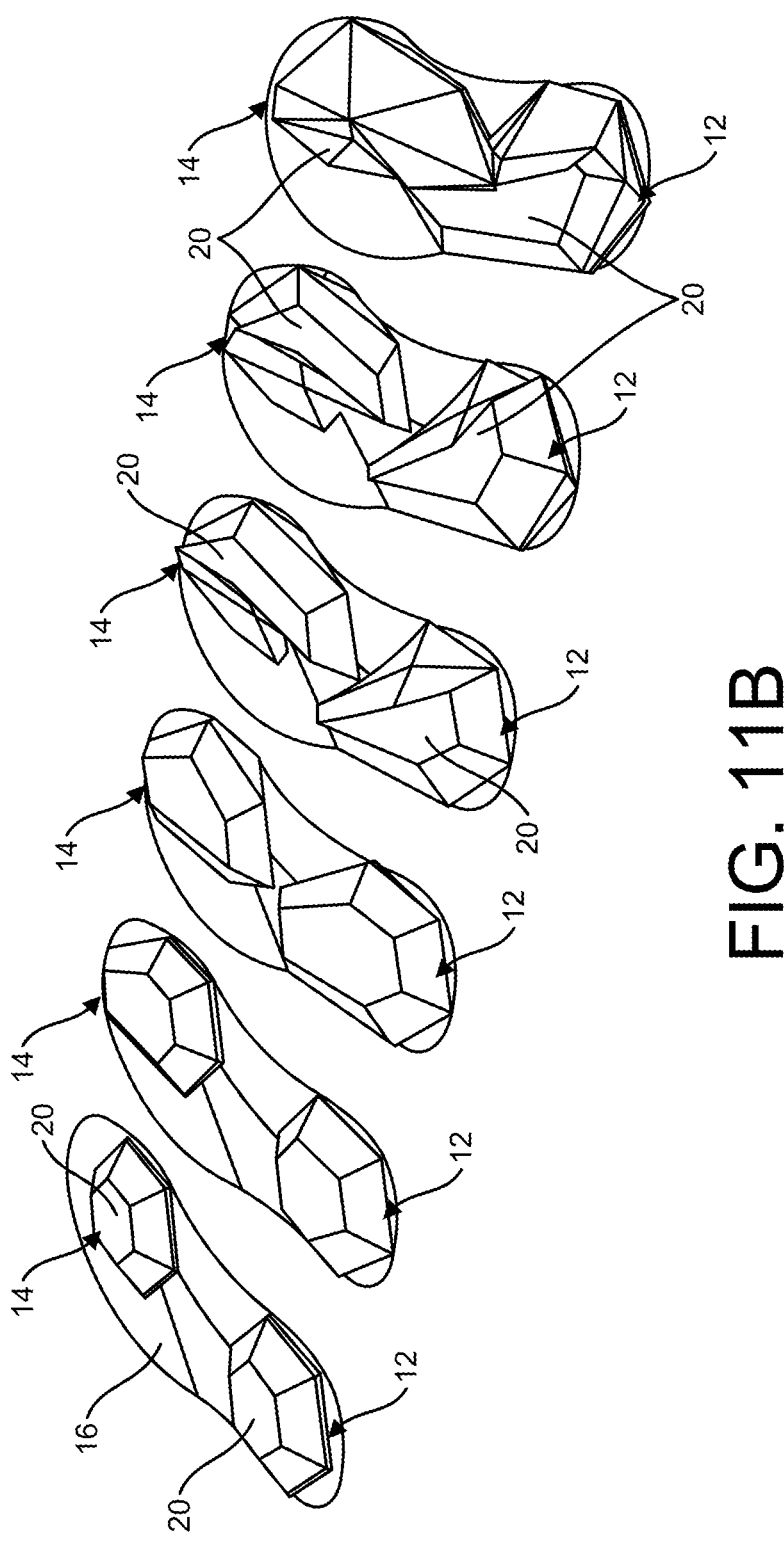
FIG. 11B illustrates a bottom perspective view of the shoe sole with some of the exemplary rectilinear projections of FIG. 11A.
Figure 11C:
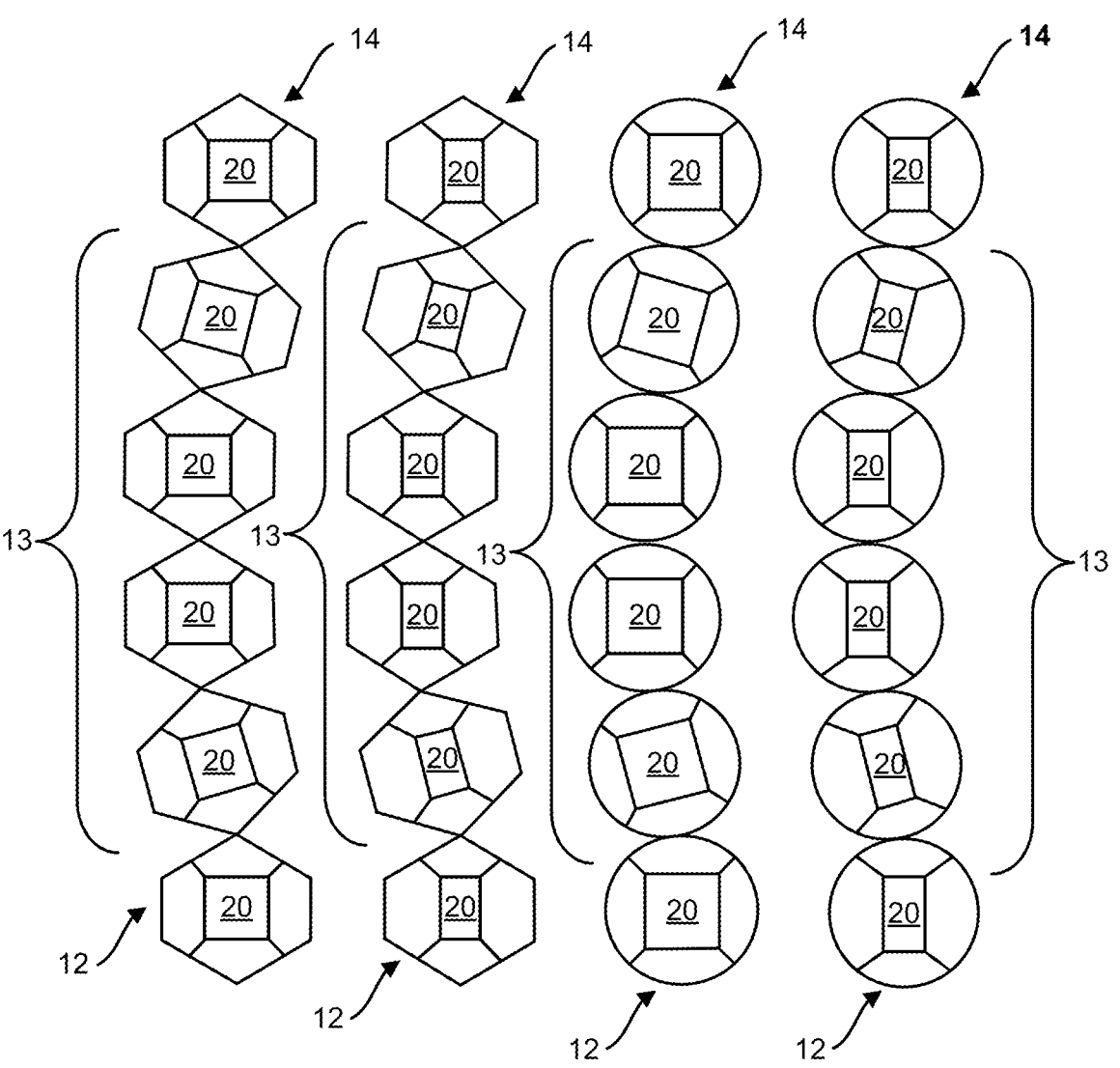
FIG. 11C illustrates a bottom view of a plurality of differing exemplary gait modification/treatment apparatuses, systems and methods according the present disclosure comprising exemplary linked rectilinear projections that extend from the hindfoot to the forefoot.

As shown in FIG. 11C, in some embodiments the gait modification/treatment device, apparatus, system and/or method 10 comprises the use of a hindfoot projection 12, a forefoot projection 14 and one or more intermediate projections 13 positioned between the hindfoot and forefoot projections 12, 14 along the anterior-posterior direction. The one or more intermediate projections 13 positioned between the hindfoot and forefoot projections 12, 14 may also be positioned medially or laterally from the hindfoot projection 12 and/or the forefoot projection 14, as shown in FIG. 11C. As shown in FIG. 11C, a plurality of intermediate projections 13 may be positioned between the hindfoot and fore-foot projections 12, 14 along the anterior-posterior direction.

The hindfoot projection 12, the forefoot projection 14 and the one or more intermediate projections 13 act to guide foot trajectory and inclination, control the direction of ground reaction forces, and provide instability during gait. The engagement surfaces 20 of the hindfoot projection 12, forefoot projection 14 and one or more intermediate projections 13 can define a center of pressure path in the anterior-posterior and medial-lateral directions via the pathway or configuration of the arrangement, placement or positioning and configuration of the hindfoot projection 12, forefoot projection 14 and one or more intermediate projections 13 (and the engagement surfaces 20 thereof). The configuration of the engagement surfaces 20 of the hindfoot projection 12, forefoot projection 14 and one or more intermediate projections 13 and the relief surfaces extending therefrom can also define the amount of instability in the varus-valgus direction, such as via the medial-lateral width of the engagement surfaces 20.

As shown in FIG. 11C, the hindfoot projection 12, the forefoot projection 14 and the one or more intermediate projections 13 may include anterior and posterior relief surfaces extending from the engagement surfaces 20 to the base of each respective projection. The hindfoot projection 12, the forefoot projection 14 and the one or more intermediate projections 13 may be separate and distinct projections, or physically linked or coupled to each other. For example, in some embodiments the hindfoot projection 12, the forefoot projection 14 and the one or more intermediate projections 13 may be separate and distinct projections that are spaced from one or more adjacent or neighboring projection, or abut one or more adjacent projection but not physically coupled thereto. Alternatively, as another example, one or more adjacent projections of the hindfoot projection 12, the forefoot projection 14 and the one or more intermediate projections 13 may be physically coupled or chained together. For example, a connector (not shown) may physically couple adjacent projections. In some embodiments, the connector may allow relative movement between the coupled projections, such as rotation therebetween at anterior and posterior ends of each projection.

Figure 10:
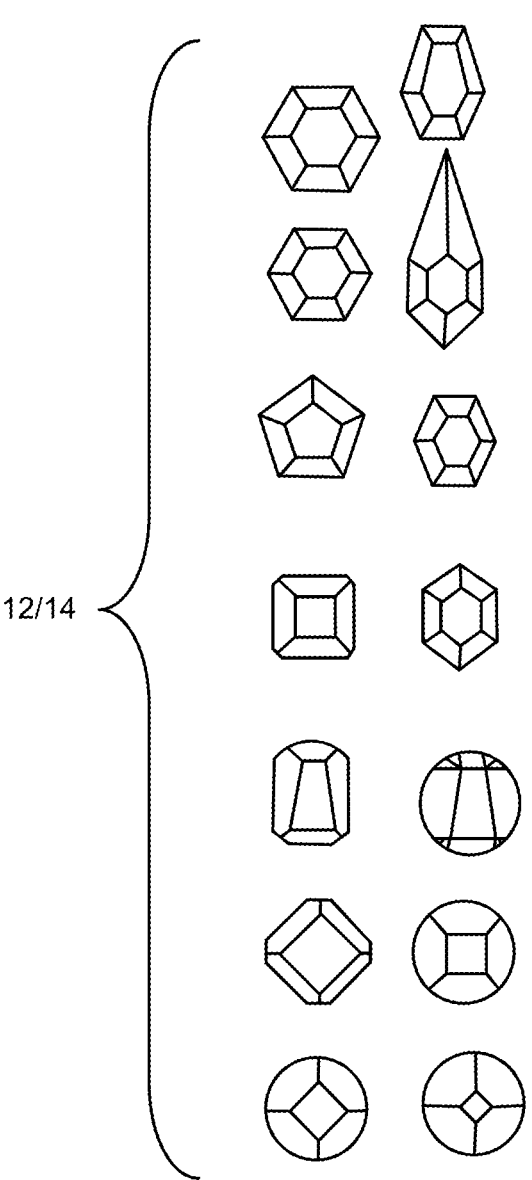
FIG. 10 illustrates a bottom view of a plurality of differing exemplary hindfoot and/or forefoot rectilinear projections of a gait modification/treatment apparatus, system and method according the present disclosure.

Exemplary regular, irregular, symmetric and asymmetric hindfoot projections 12 and/or forefoot projections 14 are shown in FIGS. 10-11C. As noted above, these configurations are only exemplary as the number, configuration and orientation of the side/relief surfaces, and the configuration and orientation of the engagement surface 20, may be chosen based on a particular patient (or shoe 18), a desired trajectory of the foot, the direction of ground reaction forces and/or a desired instability during at least a portion of one or more phase of the gait cycle. Still further, the hindfoot projections 12 and/or forefoot projections 14 may be positioned anywhere along the respective hindfoot and forefoot portions of the underside 16 of a shoe 18 in any orientation to affect the trajectory, ground reaction forces and/or instability during a person's gait cycle.

In some embodiments, the hindfoot projection 12 and/or forefoot projections 14 may project from the underside 16 of a shoe 18 such that the outer surfaces thereof (the relief/guide surfaces and the engagement surface 20) are exposed to contact a ground surface, as shown in FIGS. 1, 7-9 and 11B. Although not shown, in other embodiments, the hindfoot projection 12 and/or forefoot projections 14 may be at least partially covered or provided in a more compliant material or matrix (i.e., a material that relatively easily deforms while being walking upon during gait such that the projections 12, 14 determine the orientation and trajectory of the foot during gait cycle, determine the direction of ground reaction forces and provide instability during a gait). The compliant material may be formed via any process, such as additive or molding techniques. The compliant material may provide a more conventional external appearance to the sole of the shoe 18 than the projections 12, 14 being fully exposed. For example, the compliant material, or the compliant material and the engagement surfaces 20 of the hindfoot and/or forefoot projections 12, 14 in cooperation, may form a flat, consistent or conventionally shaped bottom surface or sole of the shoe 18, while maintaining the biomechanical and instability effects of the projections 12, 14.

FIGS. 12-26 illustrate further embodiments of an exemplary gait modification/treatment device, apparatus, system and/or method 110 that modifies the gait of a user or person by guiding the respective foot of the user to control the trajectory, center of pressure, direction of ground reaction forces, level of instability and/or orientation of the foot during gait (and/or other static and/or dynamic loading situations). As shown in FIGS. 12-26, the gait modification/treatment device, apparatus, system and/or method 110 includes a primary projection 130 that defines a primary ground engagement surface 120. The engagement surface 120 of the projection 130 is configured to engage the ground, and thereby may be positioned furthest in the plantar direction from the underside of a shoe. The engagement surface 120 may at least partially contact or engage with a ground surface during at least the foot flat and/or mid-stance phases of a gait cycle.

The gait modification/treatment device, apparatus, system and/or method 110 may be made of any material such that it substantially retains its shape while being walked on during gait, such as a material that is typical or conventionally used in orthotics and/or shoe soles. For example, at least the primary projection 130 may be formed of multicork, EVA and/or SBR, such as with a durometer within the range of about 35 Shore A to about 80 Shore A (e.g., a durometer of about 50 Shore A or about 55 Shore A). The maximum thickness of the gait modification/treatment device, apparatus, system and/or method 110, as defined by the projection 130, measured in the dorsal-plantar direction may be within the range of about 0.2 cm to about 3 cm.

In the illustrated embodiment shown in FIGS. 12-15, the gait modification/treatment device, apparatus, system and/or method 110 may be configured as a sculptured sole. The sculptured sole 110 may be the underside of a shoe, or may be configured to be coupled (removably coupled or fixedly coupled) to the underside of a shoe. As shown in FIGS. 12-15, the projection 130 is configured such that the engagement surface 120 is planar and extends medial-to-lateral as it extends from the hindfoot to the forefoot. However, the engagement surface 120 may extend lateral-to-medial as it extends from the hindfoot to the forefoot, or may not extend along the medial-lateral direction as it extends from the hindfoot to the forefoot.

As shown in FIGS. 12-15, a hind or posterior portion of the engagement surface 120 is spaced from the hind- or posterior edge of the sole 110 in the fore or anterior direction. The posterior portion of the engagement surface 120 extends medially from the lateral edge of the sole 110 to a posterior and medial relief or guide surface 122. The posterior and medial guide surface 122 may contact the ground during the heel-strike phase of gait. In some embodiments, the posterior portion of the engagement surface 120 may not extend medially past or over the midline of the sole 110 or foot of the user. As shown in FIGS. 12-15, the engagement surface 120 may extend medially toward the medial edge of the sole 110 as it extends anteriorly. The medial edge of the fore or anterior portion of the engagement surface 120 may curve sharply to, and intersect with, the medial peripheral edge of the sole 110.

Figure 12:
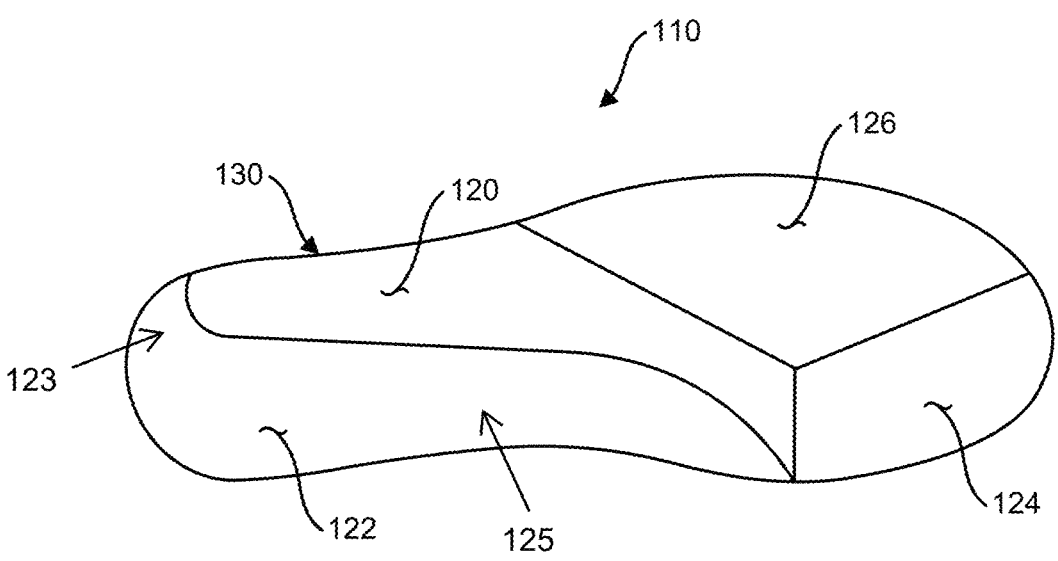
FIG. 12 illustrates a bottom view of an exemplary gait modification/treatment apparatus, system and method according the present disclosure comprising a projection for a sole that extends from the hindfoot to the forefoot.
Figure 13:
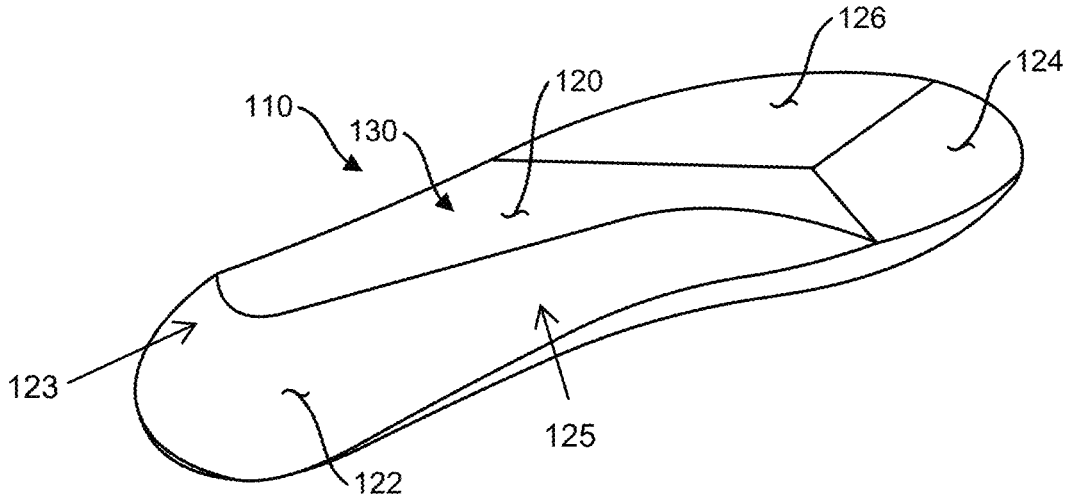
FIG. 13 illustrates a perspective view of the exemplary projection of FIG. 12.
Figure 14:
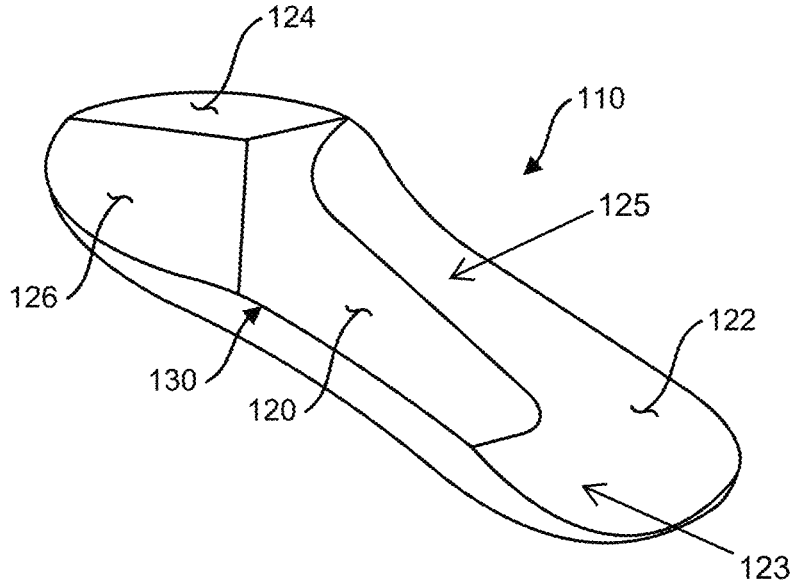
FIG. 14 illustrates another perspective view of the exemplary projection of FIG. 12.
Figure 15:
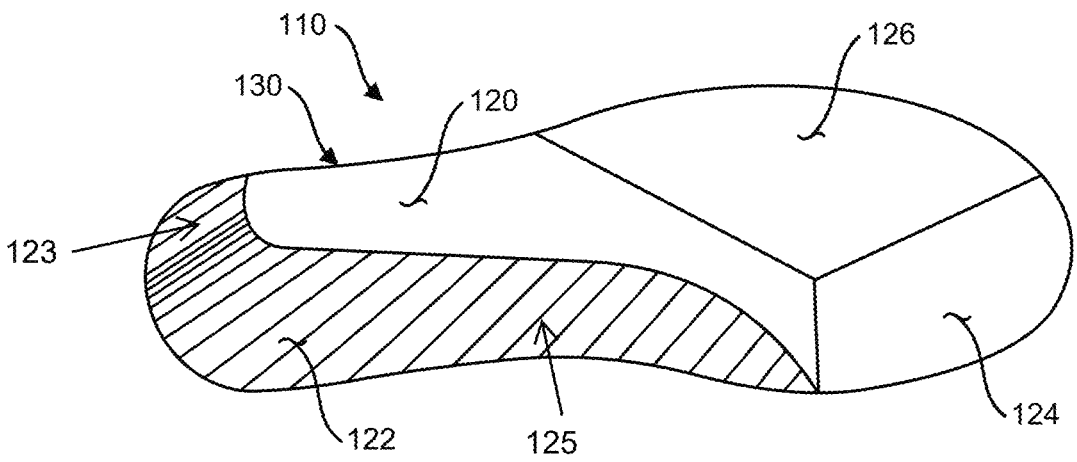
FIG. 15 illustrates a bottom view of the exemplary projection of FIG. 12.
Figures 16, 17:
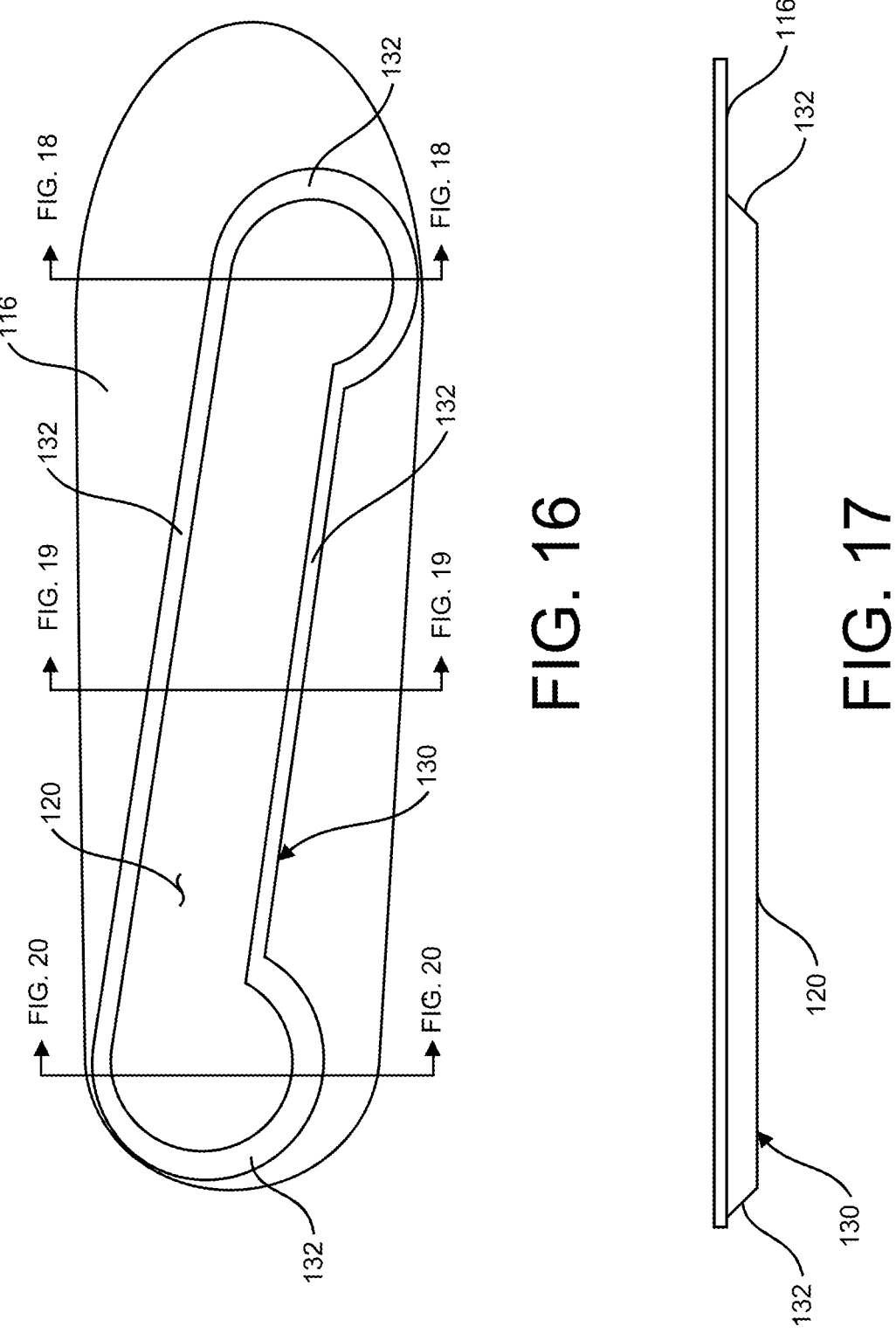
FIG. 16 illustrates a bottom view of an exemplary gait modification/treatment apparatus, system and method according the present disclosure comprising a projection for a sole that extends from the hindfoot to the forefoot.
FIG. 17 illustrates a side view of the exemplary projection of FIG. 16.
Figure 18:
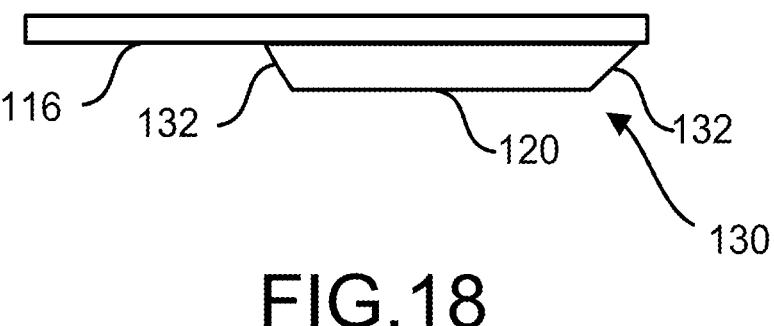
FIG. 18 illustrates a cross-sectional back view of the exemplary projection of FIG. 16.
Figure 19:
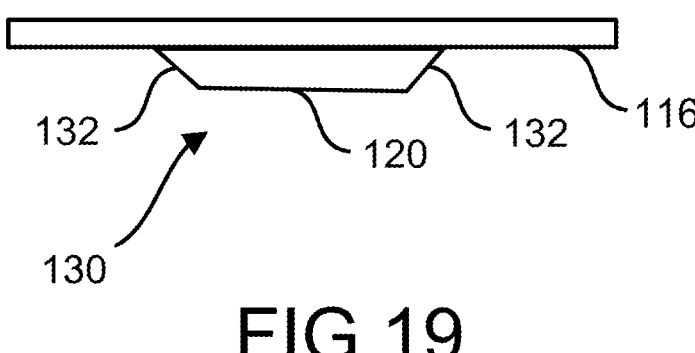
FIG. 19 illustrates another cross-sectional back view of the exemplary projection of FIG. 16.
Figure 20:
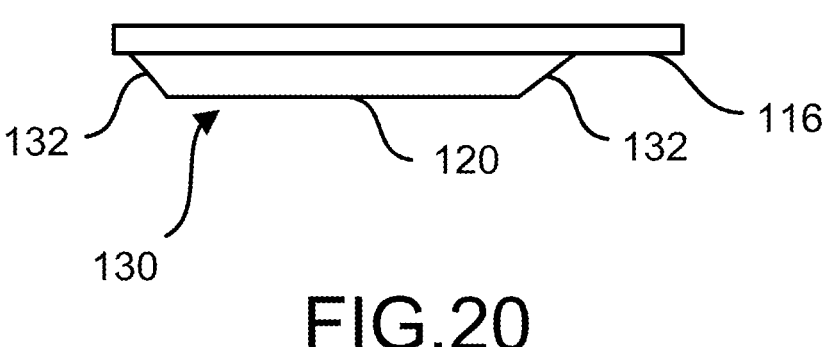
FIG. 20 illustrates another cross-sectional back view of the exemplary projection of FIG. 16.

As shown in FIGS. 12-15, a fore or anterior portion of the engagement surface 120 is spaced from the fore or anterior edge of the sole 110 in the hind or posterior direction. The anterior end portion of the engagement surface 120 extends laterally from the medial edge of the sole 110 to a lateral relief or guide surface 126. As also shown in FIGS. 12-15, the anterior end portion of the engagement surface 120 extends anteriorly to an anterior relief or guide surface 124. The anterior guide surface 124 may contact the ground during the toe-off phase of gait, as shown in FIGS. 13 and 15. In some embodiments, the anterior portion of the engagement surface 120 may not extend laterally past or over the midline of the sole 110 or foot of the user, as shown in FIGS. 13 and 15. The lateral edge of the engagement surface 120 may extend medially and posteriorly from the medial edge of the sole 110 at about the midfoot portion, as shown in FIG. 15. In some embodiments, the medially and posteriorly extending edge portion of the lateral edge of the engagement surface 120 may be linear, as shown in FIGS. 13 and 15.

As shown in FIGS. 12-14, the posterior and medial guide surface 122 may include a posterior relief surface portion 123 and a medial relief surface portion 125, and smoothly curve or arc (e.g., concavely) from the posterior and medial edges of the engagement surface 120 dorsally to the adjacent outer or peripheral edge of the sole 110. Alternatively, as shown in FIG. 15, the posterior and medial guide surface 122 may be an angled continuous facetted relief formed of a series of planar surfaces (the posterior relief surface portion 123 and the medial relief surface portion 125 being portions thereof). The lateral guide surface 126 may be a planar surface that is angled dorsally and laterally from the engagement surface 120, or may smoothly curve or arc (e.g., concavely) from the lateral and anterior edge of the engagement surface 120 dorsally and laterally to the adjacent outer or peripheral edge of the sole 110. The anterior guide surface 124 may be a planar surface that is angled dorsally and medially from the engagement surface 120, or may smoothly curve or arc (e.g., concavely) from the anterior edge of the engagement surface 120 dorsally and medially to the adjacent outer or peripheral edge of the sole 110. The posterior and medial guide surface 122, the lateral guide surface 126, and the anterior guide surface 124 may each thereby extend dorsally from the engagement surface 120 to the periphery of the adjacent or proximate edge of the sole 110. The edge or junction extending between the lateral guide surface 126 and the anterior guide surface 124 may be linear as shown in FIGS. 12-14 (and extend laterally as it extends anteriorly, for example), or alternatively be curved or arcuate.

The planar engagement surface 120 may thereby form a relatively small contact area with the ground surface during gait, thereby creating instability. If provided, the medial-lateral and/or anterior-posterior curvature or shape of the engagement surface 120 may also contribute to a particular instability. The shape or curvature of the planar engagement surface 120 thereby dictates the degree of contact with the ground surface during gait that transitions from lateral to medial during the stance phase. As discussed above, the engagement surface 120 may be angled or oriented in any direction to provide any biomechanical adjustment and/or instability profile.

As shown in FIGS. 17-20, the projection 130 may include a peripheral circumferential flat relief surface 132 that is angled dorsally and outwardly from the engagement surface 120 toward the periphery of the underside of the sole 116 of a shoe or a sole 116 configured to attach to a shoe. In an alternative embodiment, the relief surface 132 may be curved (e.g., convexly) dorsally and outwardly from the engagement surface 120 to the periphery of the underside of the sole 116 of a shoe or a sole 116 configured to attach to a shoe.

As also shown in FIGS. 17-20, the projection 130 may be configured such that the engagement surface 120 is a narrow elongate surface that is angled medially as it extends anteriorly. The engagement surface 120/projection 130 may also include a rounded bulbous or protuberant shape at its posterior and anterior ends. As shown in FIGS. 17-20, the rounded or curved shape of the bulbous posterior and anterior end portions of the engagement surface 120/projection 130 may extend further on the medial side than the lateral side thereof. Further, as also shown in FIGS. 17-20, the rounded bulbous posterior end portion of the engagement surface 120/projection 130 may be defined by a larger radius than the rounded bulbous anterior end portion thereof. The rounded bulbous posterior and anterior end portions of the engagement surface 120/projection 130 may provide or enable smooth contact transitions. Further, the projection 130 may be configured such that the engagement surface 120 includes a relatively large surface area to limit instability, or include a relatively small surface area to provide substantial instability.

Figure 21:
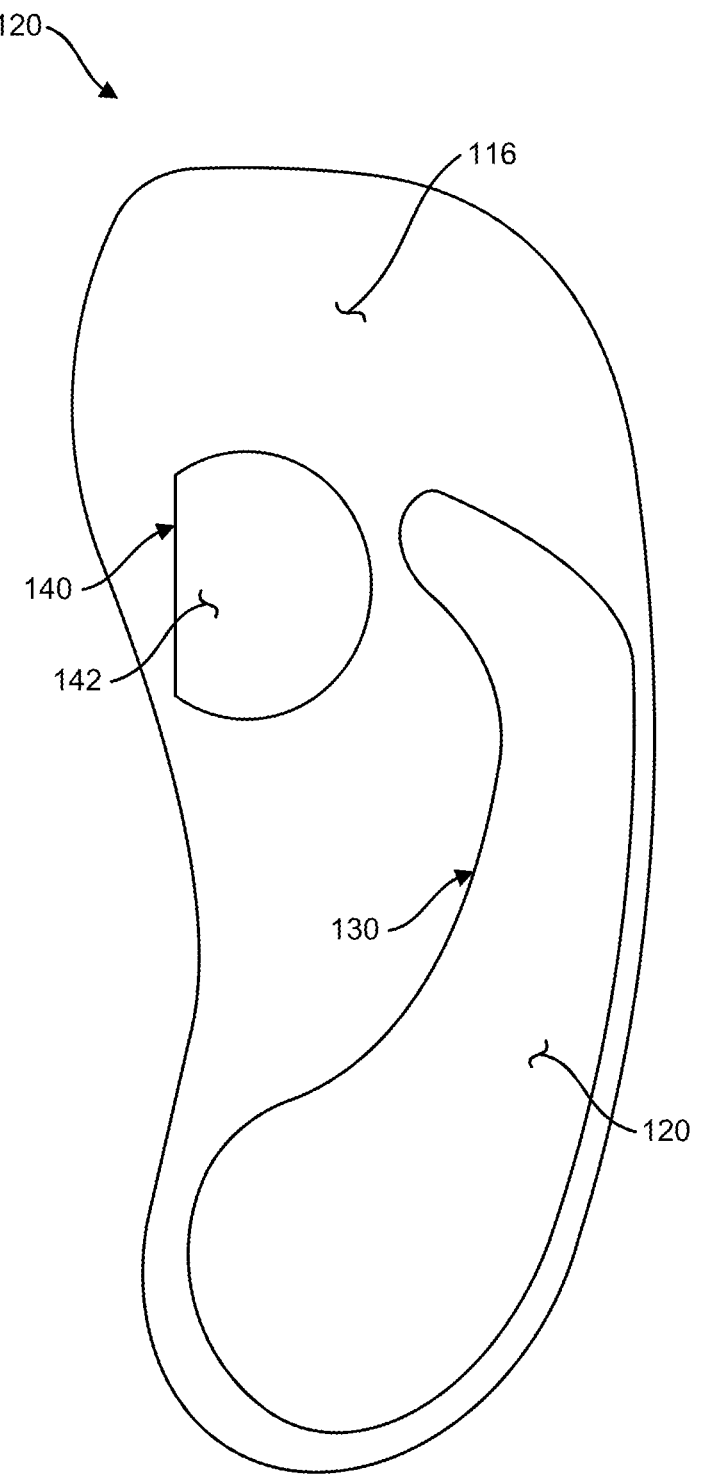
FIG. 21 illustrates a bottom view of an exemplary gait modification/treatment apparatus, system and method according the present disclosure comprising a pair of projections for a sole that extends from the hindfoot to the forefoot.

As shown in FIG. 21, in alternative embodiments the main projection 130, and thereby the main engagement surface 120, may curve laterally and then medially as it extends anteriorly from its hind or posterior portion. The anterior portion of the main projection 130, and thereby the main engagement surface 120, may curve medially at it extends to its anterior end. Further, as shown in FIG. 21, the gait modification/treatment device, apparatus, system and/or method 110 may include a secondary projection 140 that forms or defines a secondary engagement surface 142. The secondary engagement surface 142 may contact a ground surface during the toe-off phase of a gait cycle, as well as provide instability in the forefoot region. As shown in FIG. 21, the secondary projection 140/secondary engagement surface 142 may be positioned medially of the main projection 130/main engagement surface 120. The secondary projection 140/secondary engagement surface 142 may also extend further anteriorly than the main projection 130/main engagement surface 120.

As discussed above with respect to FIGS. 2-12, the main projection 130 (and potentially secondary projection 140) may be at least partially surrounded or encased within a compliant material which may form a continuous and/or flat surface plantar surface, or otherwise provide a more conventional external appearance as compared to the main projection 130 (and potentially secondary projection 140) being fully exposed.

FIGS. 22-28 illustrate further embodiments of an exemplary gait modification/treatment device, apparatus, system and/or method 210 that modifies the gait of a user or person by guiding the respective foot of the user to control the trajectory, center of pressure, direction of ground reaction forces, level of instability and/or orientation of the foot during gait (and/or other static and/or dynamic loading situations). As shown in FIGS. 22-28, the gait modification/ treatment device, apparatus, system and/or method 210 includes a rail, blade or elongate narrow projection 230 that defines an elongate narrow ground engagement surface or edge 220. The engagement surface 220 of the rail 230 is configured to engage the ground during gait. For example, the engagement surface 220 may at least partially contact or engage with the ground surface during at least the foot flat and/or mid-stance phases of a gait cycle.

Figure 22:
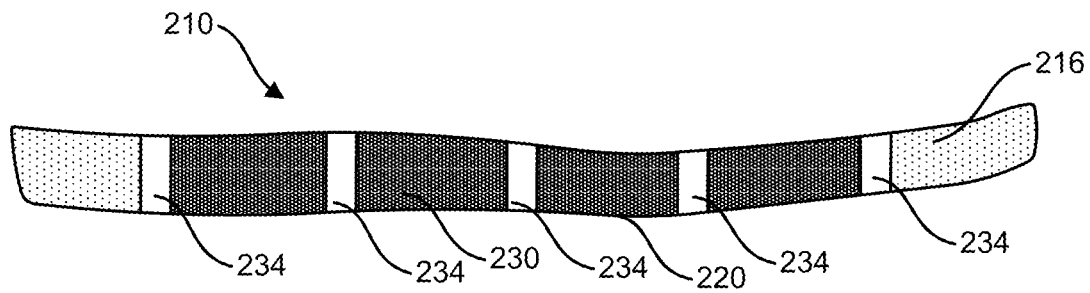
FIG. 22 illustrates a side view of an exemplary gait modification/treatment apparatus, system and method according the present disclosure comprising a shoe sole that extends from the hindfoot to the forefoot.
Figure 23:
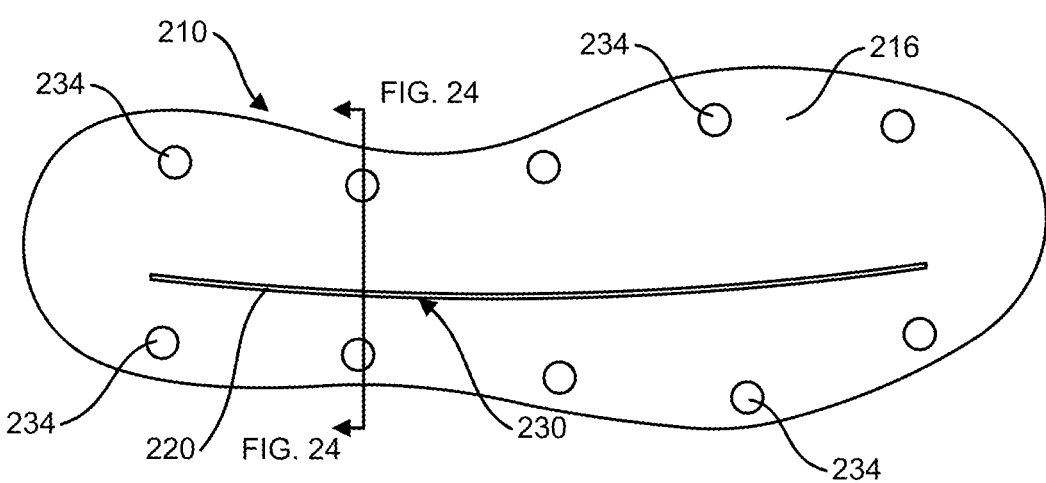
FIG. 23 illustrates a bottom view of the shoe sole of FIG. 22.

As shown in FIG. 23, the rail 230 may curve or be angled medially from a lateral portion of the hind or posterior portion of a sole 216 as it extends anteriorly to the forefoot portion of the sole 216. As shown in FIG. 22, the rail 230 may vary in height along its length in the posterior-anterior direction (e.g., the engagement surface 220 may be curved or rectilinear in the dorsal-posterior direction along its posterior-anterior length). Due to its form, the engagement surface 220 of the rail 230 is an inherently unstable ground-engaging surface during gait.

Figure 24:
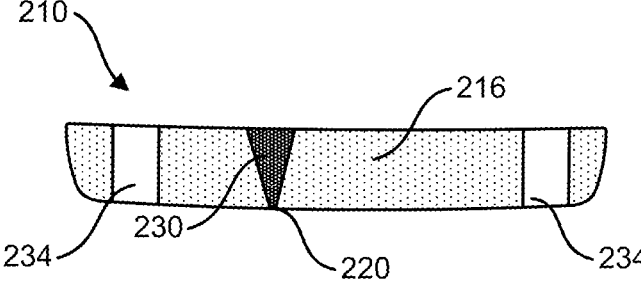
FIG. 24 illustrates a back view of the shoe sole of FIG. 22.
Figure 25:
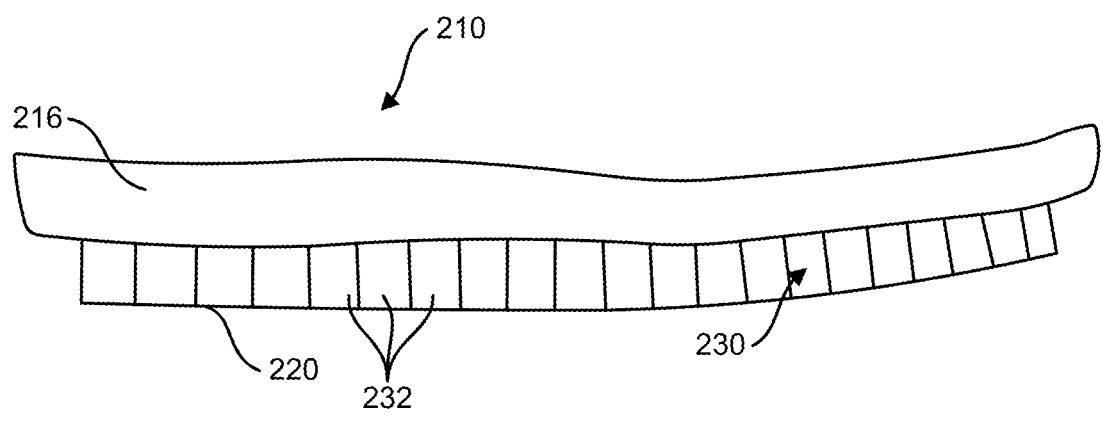
FIG. 25 illustrates a side view of the shoe sole of FIG. 23.

As discussed above, the sole 216 may be the sole of a shoe or be configured to attach to the underside or interior side of a shoe. As shown in FIGS. 23-24, the rail 230 may be encased at least partially surrounded by compliant material of the sole 216. The compliant material of the sole 216 may not interfere with the engagement surface 220 providing a primary main reaction force, trajectory of the foot and instability during gait. However, to limit instability or foot orientation, the sole 216 may include bump stops 234. The bump stops 234 may be formed of relatively stiff material that is less flexible or compressible than the compliant material of the sole 216. In some embodiments, the bump stops 234 may be substantially rigid. The sole 216 may include a plurality of bump stops 234 about the periphery of the sole 216, such as bump stops 234 that are medially, laterally, posteriorly and anteriorly spaced from the rail 230 as shown in FIG. 23. The bump stops 234 may be configured (e.g., the stiffness thereof) to allow a limited amount of instability during gait or allow a substantial amount of instability during gait.

The rail 230 may be fixedly coupled to the sole 216 as shown in FIGS. 22-24 and may be a continuous, fixed member or element. The rail 230 may also be non-adjustable while in use.

Figures 26, 27:
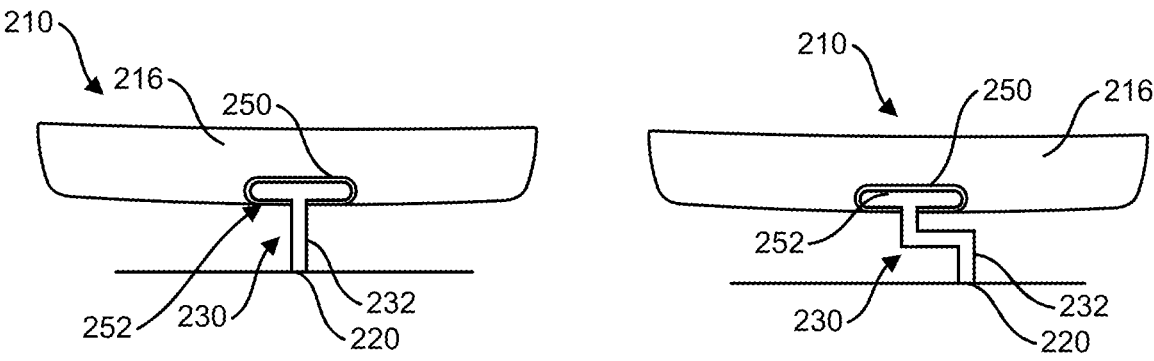
FIG. 26 illustrates a back cross-sectional view of an exemplary rail of the shoe sole of FIG. 22.
FIG. 27 illustrates a back cross-sectional view of another exemplary rail of the shoe sole of FIG. 22.
Figure 28:
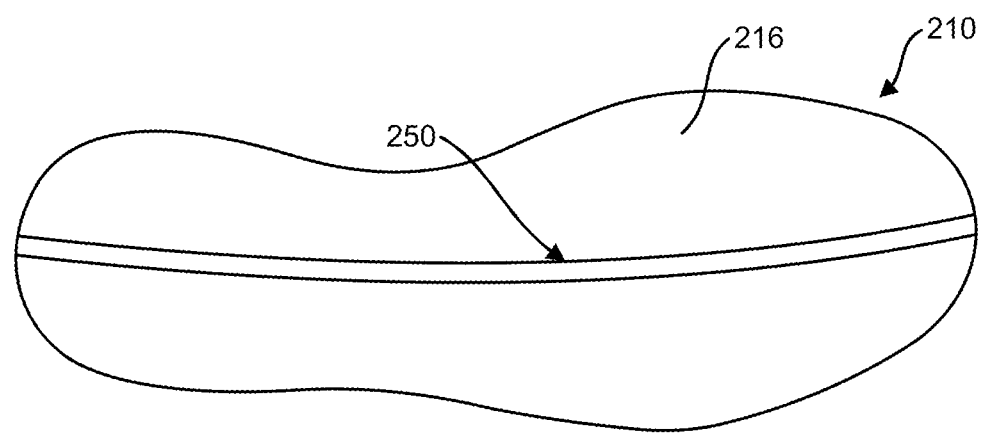
FIG. 28 illustrates a bottom view of the shoe sole of FIG. 22 with the rail portion thereof removed.

In an alternative embodiment, the rail 230 may be removably coupled to the sole 216, as shown in FIGS. 25-28. The rail 230 may include a dorsal tongue or projection 252 that is wider in the medial-lateral direction than the rail 230, as shown in FIGS. 26-28. The sole 216 may include a channel, groove or slot 250 configured to mate with or house the dorsal tongue 252 of the rail 230, as shown in FIGS. 26-28. The channel 250 within the sole 216 may include a plantar-facing opening that is narrower in the medial-lateral direction than the dorsal tongue 252, but that allows the rail 230 to extend therethrough when the dorsal tongue 252 is positioned within the channel 250, as shown in FIGS. 26 and 27. FIG. 28 shows the channel 250 within the sole 216 which may extend to at least one of the posterior or anterior edges of the sole 216 so that the dorsal tongue 252 of the rail 230 can slide into or otherwise enter the channel 250.

As shown in FIGS. 26 and 27, in some embodiments the rail 230 may be formed of modular elements 232 of different shapes. For example, some elements 232 may be of a shape such that the engagement surface 230 formed thereby is aligned with the channel 250, as shown in FIG. 26. As another example, some elements 232 may be of a shape such that the engagement surface 230 formed thereby is medially or laterally offset from the channel 250, as shown in FIG. 27.

Further, the height of the elements 232 may vary the planar position of the engagement surface 230 thereof. As yet another example, the elements 232 may be shaped such that the engagement surface 230 thereof is angled or curved in or along the medial-lateral direction and/or the dorsal-plantar direction. In this way, a plurality of different modular elements 232 may be fed into the channel 250 to form a particular engagement surface 220 of any shape, orientation, position and length to suit a particular patient (i.e., provide a desired trajectory, direction of ground reaction forces and/or instability).

As discussed above and although not shown, the rail 230 of FIGS. 22-28 may be at least partially surrounded or encased within a compliant material which may form a substantially continuous and/or flat plantar surface, or otherwise provide a more conventional external appearance as compared to the rail 230 being fully exposed.

FIGS. 29-32 illustrate further embodiments of an exemplary gait modification/treatment device, apparatus, system and/or method 310 that modifies the gait of a user or person by guiding the respective foot of the user to control the trajectory, center of pressure, direction of ground reaction forces, level of instability and/or orientation of the foot during gait (and/or other static and/or dynamic loading situations). As shown in FIGS. 29-32, the gait modification/ treatment device, apparatus, system and/or method 310 includes an array of variable stiffness or compressive pegs 360 that extend at least generally in a dorsal-plantar direction from a sole 316, and define engagement surfaces 320 at their plantar ends. The engagement surfaces 320 of the plurality of pegs 360 may be configured to engage the ground during gait. For example, at the engagement surfaces 320 of at least some of the pegs 360 may at least partially contact or engage with the ground surface during at least the foot flat and/or mid-stance phases of a gait cycle, or potentially during all ground-contact phases of the gait cycle. The engagement surfaces 320 may be planar or arcuate, such as but not limited to convex or concave.

The varied or differing stiffness or compressive nature of the array of pegs 360 may be configured to provide an unstable gait cycle. Further, the length and/or size of the pegs 360 may vary. A particular array of pegs 360 may thereby be utilized to provide a desired instability during a gait, determine the direction of ground reaction forces and/or to promote or cause a desired foot trajectory during the gait cycle. For example, the darker the shading of the pegs 360 shown in FIG. 29-31 the stiffer or less compressive the peg 360. As shown in FIGS. 29-31, in one embodiment the sole 316 includes a cluster of relative stiff pegs 360 in the hindfoot and forefoot portions at about the midline of the sole. However, any other arrangement or configuration of the array of pegs 360 may be utilized.

The diameters of the pegs 360 may be within the range from about 0.5 cm to about 2 cm. The diameters of the pegs 360 may depend or at least partially relate to the material hardness and desired stiffness of the pegs 360. The dorsal-plantar length of the pegs 360 may range from about 0.5 to about 2.0 cm.

The pegs 360 may be fixedly coupled to the sole 316, or may be removably coupled thereto as modular pegs 360. When removably coupled to the sole 316, arrays of pegs 360 of differing stiffness and/or size (e.g., length or diameter) may be utilized for each particular user or patient. In some embodiments, the pegs 360 may removably couple with the sole 316 via a snap fit cylindrical undercut, blind hole or threaded connection, for example. However, any other removable connection mechanism may be utilized. Further, a removably coupled peg 360 may be fixedly coupled to the sole 316, if desired, via an adhesive or mechanical mechanism.

The pegs 360 may be formed from any material, such as a material typically or conventionally used in shoe construction (e.g., thermoplastic rubbers, polyurethanes), and may vary in durometer within the range of about Shore A and about 80 Shore A. The material forming the pegs 360 may define, at least in part, the stiffness or compressive ability of the pegs 360. For example, the material forming the pegs 360 may naturally include a particular flexibility or compressive resistance, and the stiffness or compressive ability may be directly related to that of the material.

Figure 32:
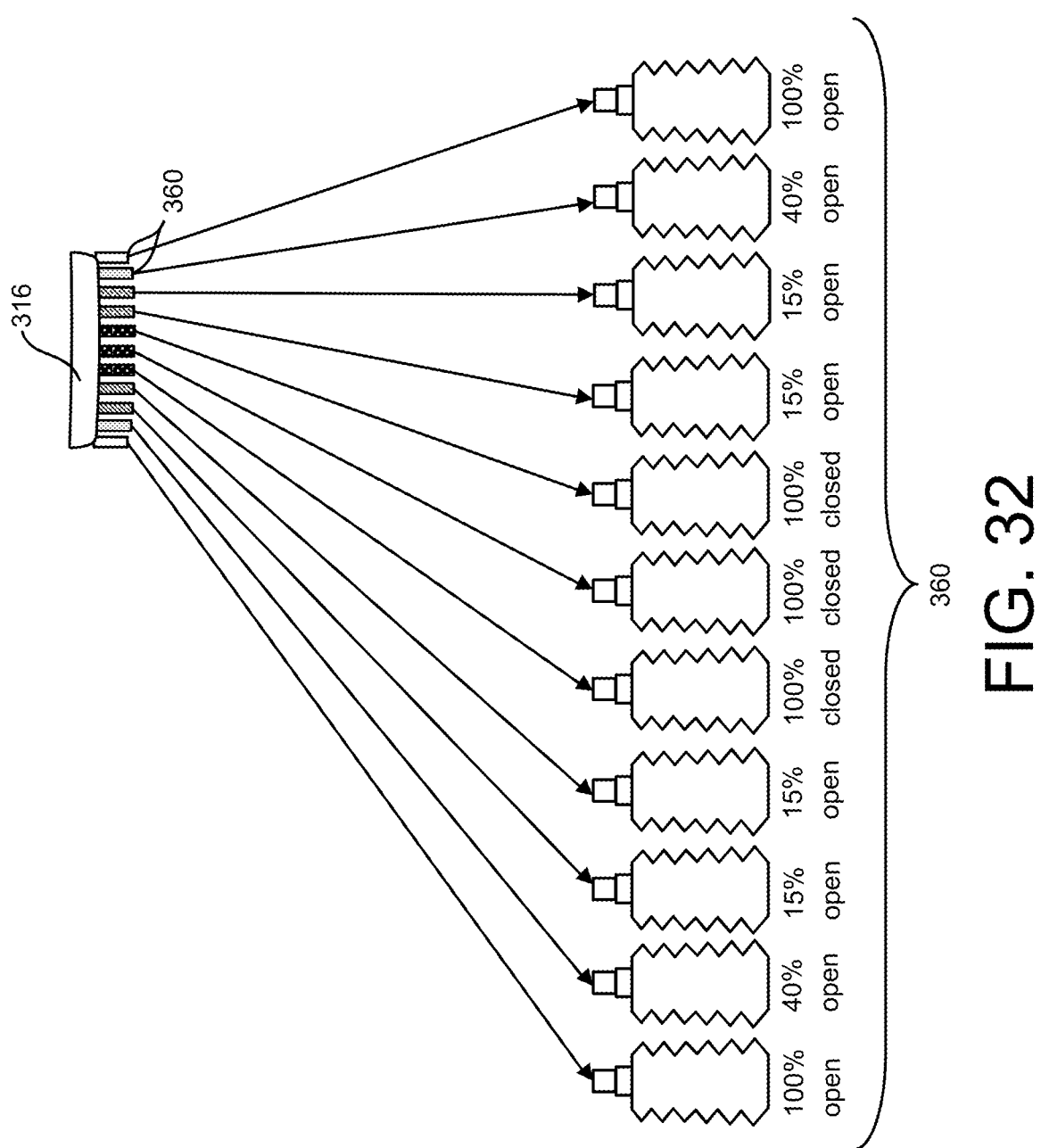
FIG. 32 illustrates a back view of the shoe sole of FIG. 29 with the pegs thereof configured as fluid controlled elements.

Alternatively, rather than the material properties of the material forming the pegs 360 defining or dictating the stiffness or compressive ability of the pegs 360, and thereby the stiffness or compressive ability of the pegs 360 being static, the pegs 360 may be configured such that their stiffness or compressive nature is adjustable. For example, as shown in FIG. 32, the at least some of the pegs 360 may include an air or fluid filled container or bladder. The pegs 360 may include a valve or other controllable or adjustable inlet/outlet mechanism to adjust the amount of material within the pegs 360 or the flow rate of material in/out of the pegs 360. In this way, the stiffness or compressive nature of the pegs 360 can be regulated by adjusting the material within the pegs 360 and/or the inlet/outlet mechanism.

In one such exemplary embodiment, as shown in FIG. 32, the pegs 360 may be formed of fluid controlled elements that are able to provide variable stiffness and load instability by adjusting of an inlet/outlet valve. As shown in FIG. 32, the pegs 360 are formed of spring bellows with an inlet/outlet valve. The bellows may be formed of any flexible material, such as but not limited to a thermoplastic molded resilient polymer such as nylon, polypropylene, polyethylene or the like. Dynamic compliance of each peg 360 can controlled by setting the level of closure of the valve. In some embodiments, the valve may be coupled to the sole 316. In such an embodiment, rotation of the anterior portions of the pegs 360 may regulate the valve to adjust the stiffness or compressive nature of the pegs 360.

As discussed above, the pegs 360 of FIGS. 29-32 may be at least partially surrounded or encased within a compliant material which may form a substantially continuous and/or flat plantar surface, or otherwise provide a more conventional external appearance as compared to pegs 360 being fully exposed.

As noted above, the gait modification or treatment apparatus, systems and methods of the present disclosure may employ a monitoring system that tracks the use/activities of the gait modification/treatment apparatus or systems of the present disclosure (and thereby the patient themselves) to improve compliance and record the nature of use to manage and adjust an individual's particularly provided/selected unstable foot-ground interface over time to enhance the effectiveness of the gait modification/treatment. The monitoring system may thereby allow individualized management of a sequence of incremental prescriptive changes via differing gait modification/treatment apparatus, systems and methods.

Figure 33:
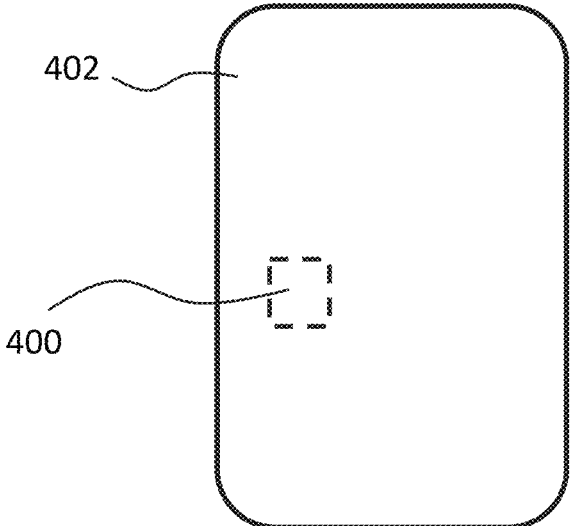
FIG. 33 illustrates a device with at least one sensor that monitors use of a gait modification or treatment apparatus.

In some such embodiments, at least one inertial measurement unit (IMU), accelerometer, load and/or pressure sensor (e.g., a pressure transducer), inclinometer or any other sensor 400, as shown in FIG. 33, may be utilized to monitor, track, record or otherwise provide data related to the activity of the user's use of the gait modification or treatment apparatus and systems disclosed herein. At least one sensor

400 may be a sensor dedicated and/or designed to monitor the user's use of the gait modification or treatment apparatus (directly and/or indirectly). At least one other sensor 400 may be a component or feature of a device that is not dedicated and/or specifically designed to monitor the user's use of the gait modification or treatment apparatus, but is configured to do so. For example, at least one sensor 400 may be a component or feature of a smartphone, smartwatch, activity tracker or other personal electronic device 402 that includes a sensor and is configured to monitor a user's use of the gait modification or treatment apparatus, as shown in FIG. 33.

A sensor may be physically associated with the user (e.g., coupled, mounted or otherwise physically linked (directly or indirectly) to the user), or may be remote or removed from the user (i.e., monitor the user without being physically linked thereto). In some embodiments, at least one sensor may be associated with a user's lower extremity (e.g., a foot, ankle, lower leg, etc.). In some embodiments, at least one sensor may be associated with and/or monitor the activity of the user's foot/feet. In some embodiments, at least one sensor may be associated with (e.g., coupled to) a user in a location other than the user's lower extremity.

The gait modification or treatment apparatus, systems and methods of the present disclosure may thereby employ a measurement device, sensor or mechanism to gather data on activity thereof, and directly and/or indirectly provide data as to the user's use of the gait modification or treatment apparatus. The activity data may be monitored and/or stored, and a gait modification method may utilize the activity data to determine a prescriptive profile that matches the needs/activity and progress of the monitored patient.

The activity data may be utilized by a gait modification method to determine a sequence or progression of less stable (i.e., provide more instability) and/or more biomechanically correcting/modifying projections, rails, pegs or other members disclosed herein that define ground engagement surfaces to change or progress a patient's gait modification or treatment. By monitoring the activity and performance level of the patient at any stage, criteria can be used to decide whether to progress to subsequent prescriptive instability and/or biomechanical correction/modification, or whether to maintain or regress, if progress is less apparent.

A gait modification method may include modifying a person's gait to reprogram that individual's patient's neuromuscular system to break away from a syndromic pathologic pattern, such as to "re-learn" a gait cycle from a state of osteo-arthritis. The gait modification method may effectively reprogram a person's gait by increasing the aggressiveness and/or variation in the instability and/or biomechanical correction/modification provided by the gait modification apparatus or system. As such, in some embodiments, a gait modification method may include significantly varying the instability and/or biomechanical correction/modification prescription each day in a manner that challenges the neuro-muscular system of the patient to reset and/or enable relearning a desired type of gait cycle.

The terminology used herein is for the purpose of describing particular embodiments only and is not intended to be limiting of an invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), "contain" (and any form contain, such as "contains" and "containing"), and any other grammatical variant thereof, are open-ended linking verbs. As a result, a method or article that "comprises", "has", "includes" or "contains" one or more steps or elements possesses those one or more steps or elements, but is not limited to possessing only those one or more steps or elements. Likewise, a step of a method or an element of an article that "comprises", "has", "includes" or "contains" one or more features possesses those one or more features, but is not limited to possessing only those one or more features.

As used herein, the terms "comprising," "has," "including," "containing," and other grammatical variants thereof encompass the terms "consisting of" and "consisting essentially of".

The phrase "consisting essentially of" or grammatical variants thereof when/if used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed compositions or methods.

Any publication cited in this specification are herein incorporated by reference as if each individual publication were specifically and individually indicated to be incorporated by reference herein as though fully set forth. Any subject matter incorporated by reference is not considered to be an alternative to any claim limitations, unless otherwise explicitly indicated.

Where one or more ranges are referred to throughout this specification, each range is intended to be a shorthand format for presenting information, where the range is understood to encompass each discrete point within the range as if the same were fully set forth herein.

While several aspects and embodiments of the present disclosure have been described and depicted herein, alternative aspects and embodiments may be affected by those skilled in the art to accomplish the same objectives. Accordingly, this disclosure and the appended claims are intended to cover all such further and alternative aspects and embodiments as fall within the true spirit and scope of inventions of the present disclosure.

The invention claimed is:

1. A gait modification apparatus, comprising:
a sculpted sole configured for use on an underside of a shoe, the sculpted sole comprising a plantar projection that projects downwardly from the underside of the shoe, the plantar projection comprising a bottom side that comprises:
a planar ground engagement surface that extends from a hindfoot portion of the sculpted sole to into a forefoot portion of the sculpted sole; and
a plurality of upwardly inclined relief surfaces that extend upwardly as the plurality of upwardly inclined relief surfaces extend contiguously from end edges of the planar ground engagement surface toward a periphery of the sculpted sole, the plurality of upwardly inclined relief surfaces comprising:
a posterior relief surface portion extending upwardly from a rear edge end of the planar ground engagement surface as the posterior relief surface portion extends rearwardly from the rear edge end toward a rear portion of the periphery of the sculpted sole;
a medial relief surface portion extending upwardly from an inner side edge end of the planar ground engagement surface as the medial relief surface portion extends from the inner side edge end toward an inner side portion of the periphery of the sculpted sole;
a planar lateral relief surface that is inclined upwardly and forwardly as the planar lateral relief surface extends from a first portion of a front edge end of the planar ground engagement surface toward an outer front portion of the periphery of the sculpted sole; and
a planar anterior relief surface that is inclined upwardly and forwardly as the planar anterior relief surface extends from a second portion of the front edge end of the planar ground engagement surface toward an inner front portion of the periphery of the sculpted sole.

2. A gait modification system, comprising:
the gait modification apparatus of claim 1; and
at least one sensor configured to monitor physical activity of a patient utilizing the gait modification apparatus to determine a gait modification prescription plan.

3. A method of modifying a gait of a patient, comprising:
coupling the gait modification apparatus of claim 1 to a plantar underside of the shoe of the patient such that the sculpted sole forms a plantar side of the shoe.

4. The method of claim 3, further comprising associating at least one sensor with the patient, wherein the sensor is configured to monitor physical activity of the patient.

5. The method of claim 3, further comprising determining a gait modification prescription plan of differing gait modification apparatuses based on monitored activity of the patient.

6. The method of claim 5, further comprising replacing or modifying the gait modification apparatus according to the determined gait modification prescription plan.

7. The gait modification apparatus of claim 1, further comprising a shoe, and wherein the sculpted sole is coupled to the shoe and forms a bottom side of the shoe.

8. The gait modification apparatus of claim 7, wherein the sculpted sole is removably coupled to an underside of the shoe.

9. The gait modification apparatus of claim 7, wherein the sculpted sole is fixedly coupled to an underside of the shoe.

10. The gait modification apparatus of claim 1, wherein the sculpted sole further comprises a top side opposite the bottom side of the plantar projection, the top side being configured to couple with the underside of the shoe.

11. The gait modification apparatus of claim 1, wherein the planar ground engagement surface extends in an inner side to outer side direction as it extends from the hindfoot portion of the sculpted sole into the forefoot portion of the sculpted sole.

12. The gait modification apparatus of claim 1, wherein the planar ground engagement surface extends to an outer side portion of the periphery of the plantar projection.

13. The gait modification apparatus of claim 1, wherein the planar ground engagement surface extends to an inner side portion of the periphery of the plantar projection.

14. The gait modification apparatus of claim 1, wherein the planar ground engagement surface is the lowest surface portion of the bottom side of the plantar projection.

15. The gait modification apparatus of claim 1, wherein at least a portion of the inner side edge end of the planar ground engagement surface extends arcuately inwardly as it extends forwardly.

16. The gait modification apparatus of claim 1, wherein the planar ground engagement surface is oriented normal to the upward-to-downward direction.

17. The gait modification apparatus of claim 1, wherein the posterior relief surface portion extends upwardly and rearwardly from the rear edge end of the planar ground engagement surface to the rear portion of the periphery of the sculpted sole.

18. The gait modification apparatus of claim 1, wherein the posterior relief surface portion comprises a continuous arcuate surface.

19. The gait modification apparatus of claim 1, wherein the posterior relief surface portion comprises a plurality of planar surfaces.

20. The gait modification apparatus of claim 1, wherein the medial relief surface portion extends upwardly and inwardly from the inner side edge end of the planar ground engagement surface to the inner side portion of the periphery of the sculpted sole.

21. The gait modification apparatus of claim 1, wherein the medial relief surface portion is inclined upwardly and rearwardly as it, from the inner side edge end of the planar ground engagement surface toward the inner side portion of the periphery of the sculpted sole.

22. The gait modification apparatus of claim 1, wherein the medial relief surface portion comprises a continuous arcuate surface.

23. The gait modification apparatus of claim 1, wherein the medial relief surface portion comprises a plurality of planar surfaces.

24. The gait modification apparatus of claim 1, wherein the planar lateral relief surface extends to the outer front portion of the periphery of the sculpted sole.

25. The gait modification apparatus of claim 1, wherein the first portion of the front edge end of the planar ground engagement surface extends forwardly, and inwardly toward the inner side portion of the periphery of the sculpted sole as it extends forwardly.

26. The gait modification apparatus of claim 1, wherein the planar lateral relief surface extends forwardly of the second portion of the front edge end of the planar ground engagement surface.

27. The gait modification apparatus of claim 1, wherein the planar anterior relief surface extends to the inner front portion of the periphery of the sculpted sole.

28. The gait modification apparatus of claim 1, wherein the planar lateral relief surface and the planar anterior relief surface are contiguous.

29. The gait modification apparatus of claim 28, wherein an edge at a junction between the planar lateral relief surface and the planar anterior relief surface extends anteriorly forwardly, and upwardly and outwardly in a direction toward an outer side portion of the periphery of the sculpted sole as the edge extends forwardly.

30. The gait modification apparatus of claim 1, wherein a rear end of the planar lateral relief surface is positioned rearwardly of a rear end of the planar anterior relief surface.

31. The gait modification apparatus of claim 1, wherein a front end of the planar anterior relief surface is positioned forwardly of a front end of the planar lateral relief surface.

32. The gait modification apparatus of claim 1, wherein the rear edge end of the planar ground engagement surface extends inwardly toward the inner side portion of the periphery of the sculpted sole, and the inner side edge end of the planar ground engagement surface extends forwardly.

33. The gait modification apparatus of claim 1, wherein the planar ground engagement surface comprises a curved edge end that extends between the rear edge end and the inner side edge end of the planar ground engagement surface.

34. The gait modification apparatus of claim 1, wherein the sculpted sole is configured such than an inner side of the sculpted sole is positioned at an inner side of the shoe, and an outer side of the sculpted sole is positioned at an outer side of the shoe, when the sculpted sole is used on the underside of the shoe.

* * * * *